United States Patent
Cahoon et al.

(12)

(10) Patent No.: US 6,348,339 B1
(45) Date of Patent: Feb. 19, 2002

(54) ENZYMES INVOLVED IN DEGRADATION OF BRANCHED-CHAIN AMINO ACIDS

(75) Inventors: Rebecca E. Cahoon; William D. Hitz; Anthony J. Kinney; J. Antoni Rafalski, all of Wilmington, DE (US)

(73) Assignee: E.I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/364,230

(22) Filed: Jul. 29, 1999

Related U.S. Application Data

(60) Provisional application No. 60/094,990, filed on Jul. 31, 1998.

(51) Int. Cl.[7] .................. C12N 9/04; C12N 1/21; C12N 5/04; C12N 1/19; C07H 21/04
(52) U.S. Cl. ................. 435/190; 435/252.3; 435/254.2; 435/410; 536/23.2; 800/278; 800/295
(58) Field of Search .................. 435/190, 252.3, 435/254.2, 410; 536/23.2; 800/278, 295

(56) References Cited

PUBLICATIONS

Hawes, John W. et al. (1996) FEB 389: 263–267.
Anderson, D.H. and Rodwell, V. W. (1989) J. Bacteriol. 171:6468–6472.
Hruz, P. W. et al., (1992) Biochemistry 31:6842–6847.
Rougraff, P.M. et al. (1989) J. Biol. Chem. 264:5899–5903.
Steele, M. I. et al., (1992) J. Biol. Chem. 267:13585–13592.
Matsubara et al., (1989) J. Biol. Chem. 264(27): 16321–16331.
NCBI General Identifier No. 4155128.
Nature 397, 176–180, (1999).
NCBI General Identifier No. 2982783.
Nature 392, 353–358 (1998).
NCBI General Identifier No. 416873.
NCBI General Identifier No. 3426048.
NCBI General Identifier No. 3759876.
NCBI General Identifier No. 3759875.
NCBI General Identifier No. 4995051.
Plant Mol. Biol. 39, 1275–1282, (1999).
NCBI General Identifier No. 1854100.
NCBI General Identifier No. 4881107.
NCBI General Identifier No. 2311971.
NCBI General Identifier No. 428577.
NCBI General Identifier No. 3767870.

*Primary Examiner*—Elizabeth Slobodyansky
(74) *Attorney, Agent, or Firm*—Inna Y. Belopolsky, Esq.

(57) ABSTRACT

This invention relates to an isolated nucleic acid fragment encoding a branched-chain amino acid degradation enzymes. The invention also relates to the construction of a chimeric gene encoding all or a portion of the branched-chain amino acid degradation enzymes, in sense or antisense orientation, wherein expression of the chimeric gene results in production of altered levels of the branched-chain amino acid degradation enzymes in a transformed host cell.

11 Claims, No Drawings

SEQUENCE LISTING

<160> NUMBER OF SEQ ID NOS: 34

<210> SEQ ID NO 1
<211> LENGTH: 745
<212> TYPE: DNA
<213> ORGANISM: Zea mays
<220> FEATURE:
<221> NAME/KEY: unsure
<222> LOCATION: (732)
<220> FEATURE:
<221> NAME/KEY: unsure
<222> LOCATION: (741)

<400> SEQUENCE: 1

```
tggcatccaa cctcatcaag gcaggctgcg acgtcacggt ttggaacagg accaagagca      60
agtgcgatcc cctcctcagt ctcggtgcca agtacgagcc tacaccggcc caagtcgctt     120
catcttgtga cgtgacattc gcgatgctcg ctgatccaca aagcgcggct gaggttgcat     180
gtgggtccag tggagctgct gaagggttgg cccctgggaa aggctatgtc gatgtgtcga     240
cggttgatgg tgctacatcc aagctgattg gtgaacgcat tacaagtact ggagcatctt     300
tccttgaggc tccagtttca ggctcgaaaa aaccagcaga agatgggctg ctcatctttc     360
ttactgcagg tgatgagtcc ttgtacaaga gagtggcgcc cctccttgat gtcatgggga     420
agtcaaggtt ttatcttggc gatgtaggca atggtgctgc aatgaagctc gtggttaaca     480
tggtcatggg gagcatgatg gtttccttct cagaagggtt gctcctgagt gaaaaagtcg     540
gtttagaccc gaatactctc gtcgaggtta tttcccaggg tgctatcagt gccccatgt     600 tctctctcaa gggcccatcc atggttaaag ctgcatatcc tcctgcattt cctctgaagc     660
atcaacagaa ggacttgagc tccattggcc tggcggatcg tgtccagtca atccacagtt     720
cagctgcaac anctgtaaag ntgca                                          745
```

<210> SEQ ID NO 2
<211> LENGTH: 247
<212> TYPE: PRT
<213> ORGANISM: Zea mays
<220> FEATURE:
<221> NAME/KEY: UNSURE
<222> LOCATION: (244)
<220> FEATURE:
<221> NAME/KEY: UNSURE
<222> LOCATION: (247)

<400> SEQUENCE: 2

```
Ala Ser Asn Leu Ile Lys Ala Gly Cys Asp Val Thr Val Trp Asn Arg
  1               5                  10                  15

Thr Lys Ser Lys Cys Asp Pro Leu Leu Ser Leu Gly Ala Lys Tyr Glu
             20                  25                  30
```

```
Pro Thr Pro Ala Gln Val Ala Ser Ser Cys Asp Val Thr Phe Ala Met
         35                  40                  45
Leu Ala Asp Pro Gln Ser Ala Ala Glu Val Ala Cys Gly Ser Ser Gly
 50                  55                  60
Ala Ala Glu Gly Leu Ala Pro Gly Lys Gly Tyr Val Asp Val Ser Thr
 65                  70                  75                  80
Val Asp Gly Ala Thr Ser Lys Leu Ile Gly Glu Arg Ile Thr Ser Thr
                 85                  90                  95
Gly Ala Ser Phe Leu Glu Ala Pro Val Ser Gly Lys Lys Pro Ala
                100                 105                 110
Glu Asp Gly Leu Leu Ile Phe Leu Thr Ala Gly Asp Glu Ser Leu Tyr
                115                 120                 125
Lys Arg Val Ala Pro Leu Leu Asp Val Met Gly Lys Ser Arg Phe Tyr
130                 135                 140
Leu Gly Asp Val Gly Asn Gly Ala Ala Met Lys Leu Val Val Asn Met
145                 150                 155                 160
Val Met Gly Ser Met Met Val Ser Phe Ser Glu Gly Leu Leu Leu Ser
                165                 170                 175
Glu Lys Val Gly Leu Asp Pro Asn Thr Leu Val Glu Val Ile Ser Gln
                180                 185                 190
Gly Ala Ile Ser Ala Pro Met Phe Ser Leu Lys Gly Pro Ser Met Val
                195                 200                 205
Lys Ala Ala Tyr Pro Pro Ala Phe Pro Leu Lys His Gln Gln Lys Asp
                210                 215                 220
Leu Ser Ser Ile Gly Leu Ala Asp Arg Val Gln Ser Ile His Ser Ser
225                 230                 235                 240
Ala Ala Thr Xaa Val Lys Xaa
                245

<210> SEQ ID NO 3
<211> LENGTH: 1288
<212> TYPE: DNA
<213> ORGANISM: Zea mays
<220> FEATURE:
<221> NAME/KEY: unsure
<222> LOCATION: (6)
<220> FEATURE:
<221> NAME/KEY: unsure
<222> LOCATION: (28)

<400> SEQUENCE: 3
atcagncaac tctgaatacg atcactanag gcaaaatgta cgcctgcagt accggtccgg      60
aattcccggg gcacaagtgt atcgctgtgg ctgcggcgcc cggcagtccg ccacaagcac     120
acgcgcacac aggggccaag cgcctacacc tacagaggag agacaaggtc ctggccgtcc     180
gcgcgtgcgc ggaagagggg acggaggaag aaggctgcca gcaatcagag atggaggtgg     240
ggttcttggg tctgggcatc atgggcaagg caatggcgac caacctcctc cgccacggct     300
tccgcgtcac cgtctggaac aggaccctcg ccaagtgcca agagctcgcc gcgctcggcg     360
ccaccgtcgg ggagacgcct gcctccgtcg tctccaagtg cagatacacc atcgccatgc     420
tctccgaccc cagcgccgcc ctatcagtcg tcttcgacaa ggatggcgtg ctcgagcaga     480
tcggtagcgg gaagggctat gtggacatgt ccactgttga cgctgcaact tcgaccaaga     540
ttagcgaggc agtaaacaa aaagggggag ctttccttga agctccagtt tcagggagca     600
agaagccagc tgaagatggc caattggtca ttcttgctgc aggggacaag ccattgtatg     660
```

-continued

```
atggtatgat tcctgcattt gatgtactgg ggaagaagtc attctttctg ggagagattg    720
ggaatggggc aaagatgaag cttgtggtca acatggtcat gggaagtatg atgaattctt    780
tgtccgaggg actctgtttg ccgacaaaa gtgggctgag ccccaaaca cttcttgatg      840 tactggacct tggtgccatc gcaaacccaa tgttcaagct gaaggggcct acaatgctgc    900
aaggcagcta cagccctgcg tttcccctga agcatcagca aaggacatg aggttagcgc     960 ttgctctggg agatgagaac gccgtcgcca tgcccgtctc agcagctgcc aatgaggcgt   1020
tcaagaaggc gaggagcctg gggctgggag accaggattt tcggcggtc tatgaggttg    1080 tgaagggcgc gggtggttct ggatctggcc agccgtgata aaggaccat ttgtgactgt    1140 gttagcccat ttccatgccg atttgcaaca tagcgacgta cgagtacgtg tgtattcgag   1200
atttggaacc agaccatacg ttgcaaaaga ataataaat caaagagatg atgctaaaaa    1260
aaaaattaaa aagggggggc cgaaccag                                      1288
```

<210> SEQ ID NO 4
<211> LENGTH: 360
<212> TYPE: PRT
<213> ORGANISM: Zea mays

<400> SEQUENCE: 4

```
Met Tyr Ala Cys Ser Thr Gly Pro Glu Phe Pro Gly His Lys Cys Ile
  1               5                  10                  15

Ala Val Ala Ala Pro Gly Ser Pro Pro Gln Ala His Ala His Thr
             20                  25                  30

Gly Ala Lys Arg Leu His Leu Gln Arg Arg Asp Lys Val Leu Ala Val
         35                  40                  45

Arg Ala Cys Ala Glu Glu Gly Thr Glu Glu Gly Cys Gln Gln Ser
     50                  55                  60

Glu Met Glu Val Gly Phe Leu Gly Leu Gly Ile Met Gly Lys Ala Met
 65                  70                  75                  80

Ala Thr Asn Leu Leu Arg His Gly Phe Arg Val Thr Val Trp Asn Arg
                 85                  90                  95

Thr Leu Ala Lys Cys Gln Glu Leu Ala Ala Leu Gly Ala Thr Val Gly
            100                 105                 110

Glu Thr Pro Ala Ser Val Val Ser Lys Cys Arg Tyr Thr Ile Ala Met
        115                 120                 125

Leu Ser Asp Pro Ser Ala Ala Leu Ser Val Val Phe Asp Lys Asp Gly
    130                 135                 140

Val Leu Glu Gln Ile Gly Ser Gly Lys Gly Tyr Val Asp Met Ser Thr
145                 150                 155                 160

Val Asp Ala Ala Thr Ser Thr Lys Ile Ser Glu Ala Val Lys Gln Lys
                165                 170                 175

Gly Gly Ala Phe Leu Glu Ala Pro Val Ser Gly Ser Lys Lys Pro Ala
            180                 185                 190

Glu Asp Gly Gln Leu Val Ile Leu Ala Ala Gly Asp Lys Pro Leu Tyr
        195                 200                 205

Asp Gly Met Ile Pro Ala Phe Asp Val Leu Gly Lys Lys Ser Phe Phe
    210                 215                 220

Leu Gly Glu Ile Gly Asn Gly Ala Lys Met Lys Leu Val Val Asn Met
225                 230                 235                 240

Val Met Gly Ser Met Met Asn Ser Leu Ser Glu Gly Leu Cys Leu Ala
                245                 250                 255

Asp Lys Ser Gly Leu Ser Pro Gln Thr Leu Leu Asp Val Leu Asp Leu
```

-continued

```
                        260                 265                 270
Gly Ala Ile Ala Asn Pro Met Phe Lys Leu Lys Gly Pro Thr Met Leu
                275                 280                 285
Gln Gly Ser Tyr Ser Pro Ala Phe Pro Leu Lys His Gln Gln Lys Asp
            290                 295                 300
Met Arg Leu Ala Leu Ala Leu Gly Asp Glu Asn Ala Val Ala Met Pro
305                 310                 315                 320
Val Ser Ala Ala Ala Asn Glu Ala Phe Lys Lys Ala Arg Ser Leu Gly
                325                 330                 335
Leu Gly Asp Gln Asp Phe Ser Ala Val Tyr Glu Val Val Lys Gly Ala
                340                 345                 350
Gly Gly Ser Gly Ser Gly Gln Pro
            355                 360

<210> SEQ ID NO 5
<211> LENGTH: 1346
<212> TYPE: DNA
<213> ORGANISM: Oryza sativa

<400> SEQUENCE: 5
cggcggctca ctcgatcagc ctctcctcct ctctacctgc cccgcatctc gaatatttgg      60
ccagtaaagc gaaagtgaag ggtttgcaaa tcggctagca gttcagagaa atgggggtt     120
gttggatgga gggttcgttc gatggtccaa catttgggtt ggaactgtcg ccggggcctc     180
tcgtccgctg cggttcaatc tcagttggag aatgtaggat tcataggact gggaaatatg     240
ggtgcccata tggcgaggaa cctggtaatg gctggatata aagtgactgt tcatgatgtc     300
aatgagaata ccatgaagaa attctcggat gatggaattc ccacaaaact gtctccactt     360
gaagtgtcca agtctagtga tgtcgtaatt acgatgctgc cttcgtctgc ccatgtatta     420
gatgtataca atggacggaa tggtttgctt gctaatgggg gctgccttgg cccttggttg     480
tatatagatt cacccacagt tgatccacaa acatcaagga aaatatccat ggacatctca     540
agatgcactt tgaaagaaaa gaaaccctat gctgaaaaac cgatgatgct ggatgctcct     600
gttcccggag gtgttcctcc tgcagaagct gggaaactca cttttcctggt aggtggttca     660
gaagaagcat atctagcagc aaaccccctta cttctctcaa tgggcaaaaa aacaatatat     720
tgtggcgggg ctggaaatgg ctcggttgca agatttgta acaacatggc aatgggcatc     780
agcatgcttg gagtctccga agcttttgct cttggtcaga atctcggcat caaagctagc     840
gttcttacag acatattcaa ctgctcaagt gcccgctgct ggagcagtga cacatataac     900
ccagttcctg gagtaatgat ggatgtgcca tcatcgagga actatgatgg tggtttcacc     960
tccaaactaa tgaccaaaga tttggatttg gccatggcct ctgcatctgg agttggcttc    1020
aattgtccct ttggttctca ggcacttgaa atttaccgaa agctatgtgc tgatggctgt    1080
gaactcaagg acttctcatg tgcatttcgc cacaactatg ctggcaaaga tgaaaattga    1140
tcttgtagct ctgccaccta acttgccacc tgttaaaata aataaagcaa taaaagttg    1200
tgtgattgaa gtgtactcag gcaaagttgg actatccttt gtaaagtgaa ttatcttaat    1260
tgacgccttt cagcctgtaa aatcaaatcc attggctcaa agcaaagctt tctctgacat    1320
ttgtactaaa aaaaaaaaaa aaaaaa                                         1346

<210> SEQ ID NO 6
<211> LENGTH: 342
<212> TYPE: PRT
<213> ORGANISM: Oryza sativa
```

-continued

```
<400> SEQUENCE: 6

Met Gly Val Val Gly Trp Arg Val Arg Ser Met Val Gln His Leu Gly
 1               5                  10                  15

Trp Asn Cys Arg Arg Gly Leu Ser Ser Ala Ala Val Gln Ser Gln Leu
                20                  25                  30

Glu Asn Val Gly Phe Ile Gly Leu Gly Asn Met Gly Ala His Met Ala
            35                  40                  45

Arg Asn Leu Val Met Ala Gly Tyr Lys Val Thr Val His Asp Val Asn
        50                  55                  60

Glu Asn Thr Met Lys Lys Phe Ser Asp Asp Gly Ile Pro Thr Lys Leu
 65                  70                  75                  80

Ser Pro Leu Glu Val Ser Lys Ser Ser Asp Val Val Ile Thr Met Leu
                85                  90                  95

Pro Ser Ser Ala His Val Leu Asp Val Tyr Asn Gly Arg Asn Gly Leu
            100                 105                 110

Leu Ala Asn Gly Gly Cys Leu Gly Pro Trp Leu Tyr Ile Asp Ser Pro
        115                 120                 125

Thr Val Asp Pro Gln Thr Ser Arg Lys Ile Ser Met Asp Ile Ser Arg
130                 135                 140

Cys Thr Leu Lys Glu Lys Lys Pro Tyr Ala Glu Lys Pro Met Met Leu
145                 150                 155                 160

Asp Ala Pro Val Pro Gly Gly Val Pro Pro Ala Glu Ala Gly Lys Leu
                165                 170                 175

Thr Phe Leu Val Gly Gly Ser Glu Glu Ala Tyr Leu Ala Ala Asn Pro
            180                 185                 190

Leu Leu Leu Ser Met Gly Lys Lys Thr Ile Tyr Cys Gly Gly Ala Gly
        195                 200                 205

Asn Gly Ser Val Ala Lys Ile Cys Asn Asn Met Ala Met Gly Ile Ser
        210                 215                 220

Met Leu Gly Val Ser Glu Ala Phe Ala Leu Gly Gln Asn Leu Gly Ile
225                 230                 235                 240

Lys Ala Ser Val Leu Thr Asp Ile Phe Asn Cys Ser Ser Ala Arg Cys
                245                 250                 255

Trp Ser Ser Asp Thr Tyr Asn Pro Val Pro Gly Val Met Met Asp Val
            260                 265                 270

Pro Ser Ser Arg Asn Tyr Asp Gly Gly Phe Thr Ser Lys Leu Met Thr
        275                 280                 285

Lys Asp Leu Asp Leu Ala Met Ala Ser Ala Ser Gly Val Gly Phe Asn
290                 295                 300

Cys Pro Phe Gly Ser Gln Ala Leu Glu Ile Tyr Arg Lys Leu Cys Ala
305                 310                 315                 320

Asp Gly Cys Glu Leu Lys Asp Phe Ser Cys Ala Phe Arg His Asn Tyr
                325                 330                 335

Ala Gly Lys Asp Glu Asn
            340

SEQ ID NO 7

LENGTH: 1282
TYPE: DNA

ORGANISM: Glycine max

SEQUENCE: 7
```

```
gcacgaggtg gtgtaggtga agtgcaatct gtgttgatgc gttccacgtt ttgctgtcac        60
ttgaaccttt cacccgtcat gattatgaag ggcttctctg ctcccatttc atcatatgtt       120
tcgcctcgag ctcaagccgt cactgagcca ccggcgcgga ttggctttt gggcctcgga        180
atcatgggct ccccaatggc ccacaatctc cttaaagctg gtgttgatct cactgtttgg       240
aataggacca agagcaagtg tgaccctcta atcagcctcg agcaaaata taaaccatct        300
cctgaggaag tagcagcatc ttgtgatgtc acctttgcca tgctcgctga tcctcaaagt       360
gcagtggatg tcgcttgcgg gaagcatggg gctgcaaatg gaatgggtcc agggaaagga       420
tatgtggatg tttcaactgt tgatggggac acttctaaat tgattaatgg cacatgaaa        480
tccactggag ccttattttt ggaggctcca gtttccggat caaaaaagcc agcagaagat       540
ggacaattga tatttcttac agcagggggac aaaaatcttt atgaagcagt tggttctctc     600
ttggacatca tggggaaatc taaattttat cttggtgatg ttggaaatgg agctgcaatg      660
aaacttgttg tcaatatgat catgggcagt atgatggcat cctttctga aggcttactt       720
ctcagcgaga aagttgggct tgatccagat gtgctagtgc aggtagtttc acagggtgcc      780
attagtgctc caatgtactc aaccaaaggt ccttccatga tacagtcgct ttatccaact      840
gcgttccctc taaagcatca gcagaaggat ctaagactag ccttgggggtt agcagagtct   900
gtttcccaac ctactccgat tgcatcagct gctaatgagt tatataaagt tgcaaaatcc     960
aatggcctta gtgatcagga ttttttcagct gtcattgaag cattaaaatc caaatttcag    1020
cactcggaaa ccaagtgaca ttcttatgag agacaagttg aagttgaaaa ccgtagtaag    1080
ctaggtgata tgaatcaaat atagacgtac attgtgaggc ttgaccattt aaattcattc    1140
cctgaattgt agaaatatat ttgaatattt ttccaatgtt gtaaattttt ggttaaaaa     1200
ttgttttcaa tgaacatctc gtatagatgt tctcctctta aaaaaaaaaa aaaaatactt    1260
gaggggggtgc ccgcctgagt ta                                            1282
```

SEQ ID NO 8
LENGTH: 345
TYPE: PRT
ORGANISM: Glycine max

SEQUENCE: 8

```
Ala Arg Gly Gly Val Gly Glu Val Gln Ser Val Leu Met Arg Ser Thr
  1               5                  10                  15

Phe Cys Cys His Leu Asn Leu Ser Pro Val Met Ile Met Lys Gly Phe
                 20                  25                  30

Ser Ala Pro Ile Ser Ser Tyr Val Ser Pro Arg Ala Gln Ala Val Thr
             35                  40                  45

Glu Pro Pro Ala Arg Ile Gly Phe Leu Gly Leu Gly Ile Met Gly Ser
         50                  55                  60

Pro Met Ala His Asn Leu Leu Lys Ala Gly Val Asp Leu Thr Val Trp
     65                  70                  75                  80

Asn Arg Thr Lys Ser Lys Cys Asp Pro Leu Ile Ser Leu Gly Ala Lys
                 85                  90                  95

Tyr Lys Pro Ser Pro Glu Glu Val Ala Ala Ser Cys Asp Val Thr Phe
                100                 105                 110

Ala Met Leu Ala Asp Pro Gln Ser Ala Val Asp Val Ala Cys Gly Lys
            115                 120                 125

His Gly Ala Ala Asn Gly Met Gly Pro Gly Lys Gly Tyr Val Asp Val
        130                 135                 140
```

Ser Thr Val Asp Gly Asp Thr Ser Lys Leu Ile Asn Gly His Met Lys
145                 150                 155                 160

Ser Thr Gly Ala Leu Phe Leu Glu Ala Pro Val Ser Gly Ser Lys Lys
            165                 170                 175

Pro Ala Glu Asp Gly Gln Leu Ile Phe Leu Thr Ala Gly Asp Lys Asn
            180                 185                 190

Leu Tyr Glu Ala Val Gly Ser Leu Leu Asp Ile Met Gly Lys Ser Lys
        195                 200                 205

Phe Tyr Leu Gly Asp Val Gly Asn Gly Ala Ala Met Lys Leu Val Val
        210                 215                 220

Asn Met Ile Met Gly Ser Met Met Ala Ser Phe Ser Glu Gly Leu Leu
225                 230                 235                 240

Leu Ser Glu Lys Val Gly Leu Asp Pro Asp Val Leu Val Gln Val Val
                245                 250                 255

Ser Gln Gly Ala Ile Ser Ala Pro Met Tyr Ser Thr Lys Gly Pro Ser
            260                 265                 270

Met Ile Gln Ser Leu Tyr Pro Thr Ala Phe Pro Leu Lys His Gln Gln
            275                 280                 285

Lys Asp Leu Arg Leu Ala Leu Gly Leu Ala Glu Ser Val Ser Gln Pro
290                 295                 300

Thr Pro Ile Ala Ser Ala Ala Asn Glu Leu Tyr Lys Val Ala Lys Ser
305                 310                 315                 320

Asn Gly Leu Ser Asp Gln Asp Phe Ser Ala Val Ile Glu Ala Leu Lys
                325                 330                 335

Ser Lys Phe Gln His Ser Glu Thr Lys
            340                 345

<210> SEQ ID NO 9
<211> LENGTH: 823
<212> TYPE: DNA
<213> ORGANISM: Glycine max

<400> SEQUENCE: 9
gtttgcttca tggtggaaaa ctcctaaggc catggttgtt gttagattca tccactattg    60
atccacaaac atcaagaaac ctttctgcta cagtaactaa ttatattcta agagaaaaga   120
aaggtgactg ggaaaaacct ttcaagttgg atgctcctgt atctggaagt gttactgcag   180
ctgaagctgg gacacttact tttatggttg gtggctctga ggaagcattt cttgctgcaa   240
agcccttact cttttcaatg ggtaaaagtg caatatattg tggtggagca ggaagtggtt   300
ctgcagcaaa aatttgcaat aatttggctt tggctgtgag catgctggga atatcagaag   360
ctcttgctct aggccaatct ctaggtgttt ctgccagcac cttgacaaat atatttaatt   420
gctccagtgc tcgctgttgg agtagtgatg cttacaaccc agttcctggg ctgatggaag   480
gggtgccctc gtcaggggat tataacggag ggtttgcatc caagcttatg gcaaaagact   540
tgaatctagc agtagaatca gctaagctgg ctggatgtaa atacccacta acatcacaag   600
cgcaaaagat atatactgag ctctgcagcg ttggccatga agccaaagac ttttcatgtg   660
cttttcgcca ttattactct ggaattgacg aacctcatga tcagtaaatt aagacgttgg   720
ttgtatgcat aaaactgttg tgatcccatg cctagtatat atggcaagaa gatcaattga   780
gctcaatgaa gttgtagaaa cagttgcgag ttaaaaaaaa aaa                       823

<210> SEQ ID NO 10
<211> LENGTH: 234

```
<212> TYPE: PRT
<213> ORGANISM: Glycine max

<400> SEQUENCE: 10

Leu Leu His Gly Gly Lys Leu Leu Arg Pro Trp Leu Leu Leu Asp Ser
 1               5                  10                  15

Ser Thr Ile Asp Pro Gln Thr Ser Arg Asn Leu Ser Ala Thr Val Thr
             20                  25                  30

Asn Tyr Ile Leu Arg Glu Lys Lys Gly Asp Trp Glu Lys Pro Phe Lys
         35                  40                  45

Leu Asp Ala Pro Val Ser Gly Ser Val Thr Ala Ala Glu Ala Gly Thr
     50                  55                  60

Leu Thr Phe Met Val Gly Gly Ser Glu Glu Ala Phe Leu Ala Ala Lys
 65                  70                  75                  80

Pro Leu Leu Phe Ser Met Gly Lys Ser Ala Ile Tyr Cys Gly Gly Ala
                 85                  90                  95

Gly Ser Gly Ser Ala Ala Lys Ile Cys Asn Asn Leu Ala Leu Ala Val
            100                 105                 110

Ser Met Leu Gly Ile Ser Glu Ala Leu Ala Leu Gly Gln Ser Leu Gly
        115                 120                 125

Val Ser Ala Ser Thr Leu Thr Asn Ile Phe Asn Cys Ser Ser Ala Arg
    130                 135                 140

Cys Trp Ser Ser Asp Ala Tyr Asn Pro Val Pro Gly Leu Met Glu Gly
145                 150                 155                 160

Val Pro Ser Ser Gly Asp Tyr Asn Gly Gly Phe Ala Ser Lys Leu Met
                165                 170                 175

Ala Lys Asp Leu Asn Leu Ala Val Glu Ser Ala Lys Leu Ala Gly Cys
            180                 185                 190

Lys Tyr Pro Leu Thr Ser Gln Ala Gln Lys Ile Tyr Thr Glu Leu Cys
        195                 200                 205

Ser Val Gly His Glu Ala Lys Asp Phe Ser Cys Ala Phe Arg His Tyr
    210                 215                 220

Tyr Ser Gly Ile Asp Glu Pro His Asp Gln
225                 230

<210> SEQ ID NO 11
<211> LENGTH: 1495
<212> TYPE: DNA
<213> ORGANISM: Triticum aestivum
<220> FEATURE:
<221> NAME/KEY: unsure
<222> LOCATION: (614)
<220> FEATURE:
<221> NAME/KEY: unsure
<222> LOCATION: (633)
<220> FEATURE:
<221> NAME/KEY: unsure
<222> LOCATION: (663)
<220> FEATURE:
<221> NAME/KEY: unsure
<222> LOCATION: (679)
<220> FEATURE:
<221> NAME/KEY: unsure
<222> LOCATION: (703)..(755)

<400> SEQUENCE: 11
aaggcaagct cccgcgtctt cttcctcttc ttccgtccca atcacgagat tgggtgagtg    60
acccgcgctt ccgccgcgtc gttcgccgaa tcccgggctg acagacgagc agtcctgact   120
cctgattcag cgcacctggg agcagaagcg ggcatgggag gtgttggatg gaggagactt   180
```

-continued

```
ggttccaagc tgcggcagag atggggctgg gagagccgcc tccgcgcccg gggcttctcc    240
tctgctcctg ccgttccacc cccaccccac atggagagtg ttggattcat agggcttggg    300
aatatgggct cccacatggc aaggaacctg gtgagggctg gatacagagt gtcagttcat    360
gatataaatg aggttgccat gaagaagttc tccgacgatg gaattcccac gaagcggtcg    420
ccacttgaag tgtctgagtc gagtgatgtt gtaatcacca tgttaccttc ctctgcccat    480
gtcttagatg tatacagtgg acggaacggc ttgcttggta atggggggcg ccttggaccg    540
tggttataca tagattcatc cacagttgat cctcatacat cgagaaagat atctatggac    600
atgtcaagat gcantttaaa tgagaagaaa ggntacgccg aaaaaccgat tatgatggat    660
gcncctgtcc ccggagggnt tcctgccgca aaagtgggac acnnnnnnnn nnnnnnnnnn    720
nnnnnnnnnn nnnnnnnnnn nnnnnnnnnn nnnnnacttc tcgcaatggg caaaaagctg    780
atctactgcg gcggggctgg aaatggctcg gctgcaaagc tctgtaacaa tatggccatg    840
gccatcagca tgcttggggt ctccgaggcc tttgctcttg gtcagaatct tgggatcaaa    900
gcaagcactc tcacagatat attcaattgc tctagcgccc gctgctggag tagcgacaca    960
tataacccag ttcctggagt aatgacgggc gtgccatcgt cgaggaatta tgatggtggc   1020
ttcacctcca aattaatggc taaagatttg gatctggcca tggcctctgc atctggagtt   1080
ggcttcaaat gccccatggg ttctgaagca cttgagattt accggaagtt atgcgacgag   1140
ggctgtgaat tcaaggactt ctcatgcgca tttcgccact tttacaccgg caaggatgag   1200
aagtgatcct gtagctatcc cagcaaactc gtcaccggtc gaaataaaac aataatgttc   1260
tccaatcgat tgaatttagg tgttagttaa acagtgccca ggcaaggttg gggtctcctt   1320
tgtacatact gttagttcga tttgcttctc ggcaatcaag ttcccagatt tccttcctgt   1380
tttgaaaaat aaatctaggt accaatctgc atctctttgt acataaatgg tccatttctg   1440
tctgcttgga ctctgttcat aaagttcgtc catacccttg caaaggctg aaata           1495
```

<210> SEQ ID NO 12
<211> LENGTH: 350
<212> TYPE: PRT
<213> ORGANISM: Triticum aestivum
<220> FEATURE:
<221> NAME/KEY: UNSURE
<222> LOCATION: (154)
<220> FEATURE:
<221> NAME/KEY: UNSURE
<222> LOCATION: (176)
<220> FEATURE:
<221> NAME/KEY: UNSURE
<222> LOCATION: (184)..(201)

<400> SEQUENCE: 12

```
Met Gly Gly Val Gly Trp Arg Arg Leu Gly Ser Lys Leu Arg Gln Arg
 1               5                  10                  15

Trp Gly Trp Glu Ser Arg Leu Arg Ala Arg Gly Phe Ser Ser Ala Pro
            20                  25                  30

Ala Val Pro Pro Pro His Met Glu Ser Val Gly Phe Ile Gly Leu
        35                  40                  45

Gly Asn Met Gly Ser His Met Ala Arg Asn Leu Val Arg Ala Gly Tyr
    50                  55                  60

Arg Val Ser Val His Asp Ile Asn Glu Val Ala Met Lys Lys Phe Ser
65                  70                  75                  80

Asp Asp Gly Ile Pro Thr Lys Arg Ser Pro Leu Glu Val Ser Glu Ser
                85                  90                  95
```

```
Ser Asp Val Val Ile Thr Met Leu Pro Ser Ser Ala His Val Leu Asp
                100                 105                 110

Val Tyr Ser Gly Arg Asn Gly Leu Leu Gly Asn Gly Gly Arg Leu Gly
            115                 120                 125

Pro Trp Leu Tyr Ile Asp Ser Ser Thr Val Asp Pro His Thr Ser Arg
        130                 135                 140

Lys Ile Ser Met Asp Met Ser Arg Cys Xaa Leu Asn Glu Lys Lys Gly
145                 150                 155                 160

Tyr Ala Glu Lys Pro Ile Met Met Asp Ala Pro Val Pro Gly Gly Xaa
                165                 170                 175

Pro Ala Ala Lys Val Gly His Xaa Xaa Xaa Xaa Xaa Xaa Xaa Xaa Xaa
            180                 185                 190

Xaa Xaa Xaa Xaa Xaa Xaa Xaa Xaa Leu Leu Ala Met Gly Lys Lys
            195                 200                 205

Leu Ile Tyr Cys Gly Gly Ala Gly Asn Gly Ser Ala Ala Lys Leu Cys
        210                 215                 220

Asn Asn Met Ala Met Ala Ile Ser Met Leu Gly Val Ser Glu Ala Phe
225                 230                 235                 240

Ala Leu Gly Gln Asn Leu Gly Ile Lys Ala Ser Thr Leu Thr Asp Ile
                245                 250                 255

Phe Asn Cys Ser Ser Ala Arg Cys Trp Ser Ser Asp Thr Tyr Asn Pro
            260                 265                 270

Val Pro Gly Val Met Thr Gly Val Pro Ser Ser Arg Asn Tyr Asp Gly
        275                 280                 285

Gly Phe Thr Ser Lys Leu Met Ala Lys Asp Leu Asp Leu Ala Met Ala
    290                 295                 300

Ser Ala Ser Gly Val Gly Phe Lys Cys Pro Met Gly Ser Glu Ala Leu
305                 310                 315                 320

Glu Ile Tyr Arg Lys Leu Cys Asp Glu Gly Cys Glu Phe Lys Asp Phe
                325                 330                 335

Ser Cys Ala Phe Arg His Phe Tyr Thr Gly Lys Asp Glu Lys
            340                 345                 350

<210> SEQ ID NO 13
<211> LENGTH: 1781
<212> TYPE: DNA
<213> ORGANISM: Zea mays

<400> SEQUENCE: 13
cccagacgca acgcaaccca cccctctct gtcctctccg tcctgaactc gcgcctcgct      60
tcgtctctcc cattcccacc cgctgaagct tcaaggagct tctcgtctga gaccgagcta    120
acgagctcac cggcgggcag gatgctggcg gcgtccacca aggtcggctc taggctggcc    180
tctccgcacg cctccttgtc cgccggtgct gcggcggcgg cactggcgag ctccccgtg     240
ctgggctctg ggatgctccc aggcgccggg ttcggcgaga cggggagtca ccacgcggca    300
gacgcgccgc cggcgctgcc ttgcagttcc tcgggcgatt caaggaaata ttatcagtgg    360
aagagactgg tgaatcaaag gcagtcaacg ctagatggag gcaaagtgcc tgctgcattg    420
ggccaccatg ttttggtgc gggctgttcc tcacggaacc aacatatcta cagatatttt    480
tcatcttctc atcaagggag tatatgggcc gggagcaagg ttctacatga cctgccaggg    540
tatgtaaaaa ttgtggaagt agggccacga gatggtctac agaacgagaa ggacatcgtg    600
ccaacacctg taaggttga gcttatacga agattggcaa tctggatact gttgtggagg    660
caacgagttt gtatctcaaa atgggtacct cagttagctg atccgaagga tgttatggaa    720
```

-continued

```
gcagttcgga ctatggggggg tgtacgtttt cctgtattga ctccaaacct taagggattt    780
gaggcagcta ttgcagcagg ggcaaaagaa atcgcaatat ttgcatcagc ttctgaagga    840
ttttccaagt caaacataaa ctgcaccatt aaagagagca ttgcccgtta taatgacgtt    900
gctcttgctg cgaaagagaa agaaattcct gtccgagggt acgtttcttg tgtggttgga    960
tgcccagtag atggaccagt gccaccttca aacgtagctt atgtagcgaa agaactttat   1020
gacatgggct gctatgaggt ttcacttggt gataccattg gagtcggtac tccaggcacc   1080
gtggttccga tgcttgaggc agctatctcc gtcgttcccg tggagaagct cgctgtccac   1140
ttccacgaca cctacggcca gtccctctcg aacattctca tctctcttca gatgggagta   1200
agcgtggtgg actcctccgt cgccggcctc ggtggctgcc ccgtacgcga agggttgcgt   1260
cgggggattg tggcgacgga ggacgtagtg tacatgctca acgggctggg cgtcaagacg   1320
ggcgtcgacc tggcaaggt gatggccgcc ggcgagttca tctgcaggca cctgggacgc   1380
cagtctgggt ccaaggcagc gaccgctctg agcaaagtta ccgcgaacgc ctccaaactc   1440
tgacaattta ccatgatccc ctactgcaga taattgcagt aaaattagcg catggtaata   1500
aatagactga ggctattcaa ataaatacgg cctcggagct agtagtgagt agattttat   1560
ttatgtccat ctagctagca aaataagcgc gacactgcca acactgccgg tctagcaagc   1620
aaaatgagca aatatgtgac cacctctacg ggaaagattc ccccaacact ctcagcaaac   1680
ggaagtggtg catcagttcg ttccagcttc agtcatcac atgttcactc agcaaacaga   1740
aatggagcat cagttcgttc cagcttccaa aaaaaaaaa a                        1781
```

<210> SEQ ID NO 14
<211> LENGTH: 433
<212> TYPE: PRT
<213> ORGANISM: Zea mays

<400> SEQUENCE: 14

```
Met Leu Ala Ala Ser Thr Lys Val Gly Ser Arg Leu Ala Ser Pro His
  1               5                  10                  15

Ala Ser Leu Ser Ala Gly Ala Ala Ala Ala Leu Ala Ser Ser Pro
             20                  25                  30

Val Leu Gly Ser Gly Met Leu Pro Gly Ala Gly Phe Gly Glu Thr Gly
         35                  40                  45

Ser His His Ala Ala Asp Ala Pro Pro Ala Leu Pro Cys Ser Ser Ser
     50                  55                  60

Gly Asp Ser Arg Glu Tyr Tyr Gln Trp Lys Arg Leu Val Asn Gln Arg
 65                  70                  75                  80

Gln Ser Thr Leu Asp Gly Gly Lys Val Pro Ala Ala Leu Gly His His
                 85                  90                  95

Val Phe Gly Ala Gly Cys Ser Ser Arg Asn Gln His Ile Tyr Arg Tyr
            100                 105                 110

Phe Ser Ser Ser His Gln Gly Ser Ile Trp Ala Gly Ser Lys Val Leu
        115                 120                 125

His Asp Leu Pro Gly Tyr Val Lys Ile Val Glu Val Gly Pro Arg Asp
    130                 135                 140

Gly Leu Gln Asn Glu Lys Asp Ile Val Pro Thr Pro Val Lys Val Glu
145                 150                 155                 160

Leu Ile Arg Arg Leu Ala Ile Trp Ile Leu Leu Trp Arg Gln Arg Val
                165                 170                 175

Cys Ile Ser Lys Trp Val Pro Gln Leu Ala Asp Pro Lys Asp Val Met
```

```
                      180               185               190
Glu Ala Val Arg Thr Met Gly Gly Val Arg Phe Pro Val Leu Thr Pro
                195                 200                 205
Asn Leu Lys Gly Phe Glu Ala Ala Ile Ala Ala Gly Ala Lys Glu Ile
            210                 215                 220
Ala Ile Phe Ala Ser Ala Ser Glu Gly Phe Ser Lys Ser Asn Ile Asn
225                 230                 235                 240
Cys Thr Ile Lys Glu Ser Ile Ala Arg Tyr Asn Asp Val Ala Leu Ala
                245                 250                 255
Ala Lys Glu Lys Glu Ile Pro Val Arg Gly Tyr Val Ser Cys Val Val
            260                 265                 270
Gly Cys Pro Val Asp Gly Pro Val Pro Pro Ser Asn Val Ala Tyr Val
        275                 280                 285
Ala Lys Glu Leu Tyr Asp Met Gly Cys Tyr Glu Val Ser Leu Gly Asp
        290                 295                 300
Thr Ile Gly Val Gly Thr Pro Gly Thr Val Val Pro Met Leu Glu Ala
305                 310                 315                 320
Ala Ile Ser Val Val Pro Val Glu Lys Leu Ala Val His Phe His Asp
                325                 330                 335
Thr Tyr Gly Gln Ser Leu Ser Asn Ile Leu Ile Ser Leu Gln Met Gly
            340                 345                 350
Val Ser Val Val Asp Ser Ser Val Ala Gly Leu Gly Gly Cys Pro Val
            355                 360                 365
Arg Glu Gly Leu Arg Arg Gly Ile Val Ala Thr Glu Asp Val Val Tyr
        370                 375                 380
Met Leu Asn Gly Leu Gly Val Lys Thr Gly Val Asp Leu Gly Lys Val
385                 390                 395                 400
Met Ala Ala Gly Glu Phe Ile Cys Arg His Leu Gly Arg Gln Ser Gly
                405                 410                 415
Ser Lys Ala Ala Thr Ala Leu Ser Lys Val Thr Ala Asn Ala Ser Lys
                420                 425                 430
Leu
```

<210> SEQ ID NO 15
<211> LENGTH: 1705
<212> TYPE: DNA
<213> ORGANISM: Zea mays

<400> SEQUENCE: 15

```
gggccgcctg cgggcgggag gaagaaaagc gaagctgctg cgccctcccc tcccccatct    60
ccgcccccg  cctcacccac cagacgagag agcgagcgca gttcggccgc cggtcgcgtc   120
cgactccagc aaagccgagc gcccacccc  tcaccctatt accttcctct cgggtccaat   180
tcggtgcctg gctgactccg cacgtcttcc cccttttcc  ctccctcgac cgacgaccgt   240
ccgtccacca ccggatccag gagcgaccct ccctcgtgct cgtcgacgat cgaccggccg   300
ccgatcgtcc aggaaggatg tcgagcctcg aggagccgct gggtctcgga gacctgccta   360
agttgagtat taacagactc gggcggttcg tgtcgctggg cgctcggagg ccaccggccg   420
acgacgacga ccacagcact ggcaaataca gcagcagctc ctgcaacaat ggcagccatc   480
agatggcctt ccatcatggc agcaactcct cctatccctg gcacccgcag tgccgccagg   540
ccgccgatcc atcacgcgat gcagtggagc ttagagatct ccctcgcaag gtcatgtggg   600
agctgccgag gttcgtgaag atagtggagg tgggcctcg  ggacgccctg cagaacgaga   660
agggcaacgt cccggcgtcc gtgaagatcc agctgataca caagctggtc ggcgcgggcc   720
```

```
tgtcggttgt cgaggccacc agcttcgtct ccccaaagtg ggtgccgcag ctagccgacg      780
cagaggaggt gctgaagggt ataaagcagg agccaggcgt gcggtacccg gtgctaacac      840
ctaacctcag agggttcgag gctgccatcg cagccggcgc gaaggaaatc gcggtcttcg      900
cgtccgcgtc tgaatccttc tccaggtcca acatcaactg caccatcgag gagagccttg      960
ctcggtaccg cggcgtcaca gcggctgcca agaaacacgg gctaagcatc cggggtacg      1020 tgtcatgtgt gattgcttgc cccgttggag gcgcaaccga tccggcgaag gtggcgtacg     1080
tagctaagga gctgtatacc atgggctgct cggagatctc gctcggcgac acgactggtg     1140
tcgggacacc aggtagcgtg gttgctatgc ttcaagctgt catgtcgttt gtcccggtgg     1200
acaagattgc cgttcatttc cacgatacgt acgggcaggc ccttgccaac atcctcgtct     1260
cccttcaaat ggggatcaac atagtggact cgtcggtgtc gggccttgga ggctgcccgt     1320
atgccaaggg cgccactggc aacgtcgcca cggaggatgt cgtgtacatg ctccatggcc     1380
tggggatcga gaccaacgtc gacctcaaca agctcatgga ggctggtgac tacatctcca     1440
agcatctggg caggccgctg ggttccaaga ccgccactgc tctccgcaag ctgaccgcct     1500
gaaaaaacct tttcaagcac tcccaagaga aatgtatcgg ttcgaggtcc catctctcag     1560
tcatatgaat gtcctgtagt tttactttat gcttttttc cgctcagaca ttgcctactc      1620
tgagcatttt attcacacac tttgtacccg ccgttggatg attctgaata atcttggtgt     1680
tccaaaaaaa aaaaaaaaaa aaaat                                           1705
```

<210> SEQ ID NO 16
<211> LENGTH: 394
<212> TYPE: PRT
<213> ORGANISM: Zea mays

<400> SEQUENCE: 16

```
Met Ser Ser Leu Glu Glu Pro Leu Gly Leu Gly Asp Leu Pro Lys Leu
 1               5                  10                  15

Ser Ile Asn Arg Leu Gly Arg Phe Val Ser Leu Gly Ala Arg Arg Pro
            20                  25                  30

Pro Ala Asp Asp Asp His Ser Thr Gly Lys Tyr Ser Ser Ser Ser
        35                  40                  45

Cys Asn Asn Gly Ser His Gln Met Ala Phe His Gly Ser Asn Ser
    50                  55                  60

Ser Tyr Pro Trp His Pro Gln Cys Arg Gln Ala Ala Asp Pro Ser Arg
65                  70                  75                  80

Asp Ala Val Glu Leu Arg Asp Leu Pro Arg Lys Val Met Trp Glu Leu
                85                  90                  95

Pro Arg Phe Val Lys Ile Val Glu Val Gly Pro Arg Asp Gly Leu Gln
            100                 105                 110

Asn Glu Lys Gly Asn Val Pro Ala Ser Val Lys Ile Gln Leu Ile His
        115                 120                 125

Lys Leu Val Gly Ala Gly Leu Ser Val Val Glu Ala Thr Ser Phe Val
    130                 135                 140

Ser Pro Lys Trp Val Pro Gln Leu Ala Asp Ala Glu Glu Val Leu Lys
145                 150                 155                 160

Gly Ile Lys Gln Glu Pro Gly Val Arg Tyr Pro Val Leu Thr Pro Asn
                165                 170                 175

Leu Arg Gly Phe Glu Ala Ala Ile Ala Ala Gly Ala Lys Glu Ile Ala
            180                 185                 190
```

```
Val Phe Ala Ser Ala Ser Glu Ser Phe Ser Arg Ser Asn Ile Asn Cys
        195                 200                 205

Thr Ile Glu Glu Ser Leu Ala Arg Tyr Arg Gly Val Thr Ala Ala Ala
        210                 215                 220

Lys Lys His Gly Leu Ser Ile Arg Gly Tyr Val Ser Cys Val Ile Ala
225                 230                 235                 240

Cys Pro Val Gly Gly Ala Thr Asp Pro Ala Lys Val Ala Tyr Val Ala
                245                 250                 255

Lys Glu Leu Tyr Thr Met Gly Cys Ser Glu Ile Ser Leu Gly Asp Thr
            260                 265                 270

Thr Gly Val Gly Thr Pro Gly Ser Val Val Ala Met Leu Gln Ala Val
        275                 280                 285

Met Ser Phe Val Pro Val Asp Lys Ile Ala Val His Phe His Asp Thr
    290                 295                 300

Tyr Gly Gln Ala Leu Ala Asn Ile Leu Val Ser Leu Gln Met Gly Ile
305                 310                 315                 320

Asn Ile Val Asp Ser Ser Val Ser Gly Leu Gly Gly Cys Pro Tyr Ala
                325                 330                 335

Lys Gly Ala Thr Gly Asn Val Ala Thr Glu Asp Val Val Tyr Met Leu
            340                 345                 350

His Gly Leu Gly Ile Glu Thr Asn Val Asp Leu Asn Lys Leu Met Glu
        355                 360                 365

Ala Gly Asp Tyr Ile Ser Lys His Leu Gly Arg Pro Leu Gly Ser Lys
    370                 375                 380

Thr Ala Thr Ala Leu Arg Lys Leu Thr Ala
385                 390

<210> SEQ ID NO 17
<211> LENGTH: 1543
<212> TYPE: DNA
<213> ORGANISM: Oryza sativa

<400> SEQUENCE: 17
gcgcgagctt acacggtgct ctctcctcct ttgcgtcgga ttcaagtaag gcttgttgag     60
ttcggtgccc tatatcactc actcaatcct gggtgcgatt tgatcgggtt ggcttccaat    120
ttgtcgatcg atcgagtctt cttcacattg taacatctga ttccagaatg tcgagcctcg    180
aggagccgct cggtcttggg gaccttccaa agttgagtat taacagactt gaaaggttct    240
ctccaaatgc ttgcagagca agtgctgatg accgtagcac cagcaattac aagcatcaca    300
atggtggcaa caatcagacg atctttcaca gcagttctca ttcatggcat atgcaaggcc    360
aatatactga ttcctcctgc aatggagtgg atatggagtt cagagctctt ccacggaagg    420
ttttgtggga gcttccaagg tttgtgaaga tagttgaagt cggaccacgg gatggtctgc    480
aaaatgagaa gagtactgta ccagcttctg taaagattga actgatacac aaattggtgg    540
cttctggtct atcagtagtt gaagccacaa gttttgtttc cccaaaatgg gtgccgcagc    600
tagctgatgc aaaggatgtc cttcaaggga ttaggcatgt gccagatgtg cggtttcctg    660
tgttaactcc taacctcaga ggatttgagg ctgctcttgc agctggtgca aagaagttg    720 cagtcttcgc atctgcctct gaatcctttt ctaagtcaaa ccttaattgt accatcaagg    780
aaagccttgt tcggtaccgt gatgttgtaa cttctgccaa gaaacatgga atgcgaatcc    840
gtgggtatgt tcatgtgtg gttggttgcc ctgttgaagg cacaattcat ccatcaaagg    900
tagcatacgt agctaaggag ctttatgaca tgggttgctc ggagatttca cttggagaca    960
```

-continued

```
cgattggtgt tggtacacca ggtagcatac ttgctatgct tgaagctgta atgtcttttg      1020
ttccagtgga caagctcgcc gtccattttc atgacacata cggccaagcc cttgccaaca      1080
tactggtctc tctccaactg gggatcaaca tagtggactc atcagtgtca ggactgggag      1140
gctgcccata tgcaaagggc gccaccggca atgtcgcgac ggaggacgtt gtgtacatgc      1200
tccatggact ggggatagag accaatgttg acctcaacaa gctcatggat gctggagatt      1260
acatctccaa gcatctggga aggcagtcag gctccaagac caccactgct ctccgcaagc      1320
taaccactta gtccctgat gatcataata gggattcaga aaagaagacc gaagatacat       1380
cggttggcgt cagtttaatg tttttacaca aatcatatgt gattgtaact tgtaaaccgt      1440
ctcaatttag tcccaatatg ggtgaaagta aacagaaacc atatatgtat acacacattt      1500
gtgtttaatt tcttggattg aataaaaaaa aaaaaaaaa aaa                         1543
```

<210> SEQ ID NO 18
<211> LENGTH: 387
<212> TYPE: PRT
<213> ORGANISM: Oryza sativa

<400> SEQUENCE: 18

```
Met Ser Ser Leu Glu Glu Pro Leu Gly Leu Gly Asp Leu Pro Lys Leu
  1               5                  10                  15

Ser Ile Asn Arg Leu Glu Arg Phe Ser Pro Asn Ala Cys Arg Ala Ser
             20                  25                  30

Ala Asp Asp Arg Ser Thr Ser Asn Tyr Lys His His Asn Gly Gly Asn
         35                  40                  45

Asn Gln Thr Ile Phe His Ser Ser His Ser Trp His Met Gln Gly
     50                  55                  60

Gln Tyr Thr Asp Ser Ser Cys Asn Gly Val Asp Met Glu Phe Arg Ala
 65                  70                  75                  80

Leu Pro Arg Lys Val Leu Trp Glu Leu Pro Arg Phe Val Lys Ile Val
                 85                  90                  95

Glu Val Gly Pro Arg Asp Gly Leu Gln Asn Glu Lys Ser Thr Val Pro
            100                 105                 110

Ala Ser Val Lys Ile Glu Leu Ile His Lys Leu Val Ala Ser Gly Leu
        115                 120                 125

Ser Val Val Glu Ala Thr Ser Phe Val Ser Pro Lys Trp Val Pro Gln
    130                 135                 140

Leu Ala Asp Ala Lys Asp Val Leu Gln Gly Ile Arg His Val Pro Asp
145                 150                 155                 160

Val Arg Phe Pro Val Leu Thr Pro Asn Leu Arg Gly Phe Glu Ala Ala
                165                 170                 175

Leu Ala Ala Gly Ala Lys Glu Val Ala Val Phe Ala Ser Ala Ser Glu
            180                 185                 190

Ser Phe Ser Lys Ser Asn Leu Asn Cys Thr Ile Lys Glu Ser Leu Val
        195                 200                 205

Arg Tyr Arg Asp Val Val Thr Ser Ala Lys Lys His Gly Met Arg Ile
    210                 215                 220

Arg Gly Tyr Val Ser Cys Val Gly Cys Pro Val Glu Gly Thr Ile
225                 230                 235                 240

His Pro Ser Lys Val Ala Tyr Val Ala Lys Glu Leu Tyr Asp Met Gly
                245                 250                 255

Cys Ser Glu Ile Ser Leu Gly Asp Thr Ile Gly Val Gly Thr Pro Gly
            260                 265                 270
```

```
Ser Ile Leu Ala Met Leu Glu Ala Val Met Ser Phe Val Pro Val Asp
            275                 280                 285
Lys Leu Ala Val His Phe His Asp Thr Tyr Gly Gln Ala Leu Ala Asn
        290                 295                 300
Ile Leu Val Ser Leu Gln Leu Gly Ile Asn Ile Val Asp Ser Ser Val
305                 310                 315                 320
Ser Gly Leu Gly Gly Cys Pro Tyr Ala Lys Gly Ala Thr Gly Asn Val
                325                 330                 335
Ala Thr Glu Asp Val Val Tyr Met Leu His Gly Leu Gly Ile Glu Thr
            340                 345                 350
Asn Val Asp Leu Asn Lys Leu Met Asp Ala Gly Asp Tyr Ile Ser Lys
        355                 360                 365
His Leu Gly Arg Gln Ser Gly Ser Lys Thr Thr Thr Ala Leu Arg Lys
    370                 375                 380
Leu Thr Thr
385

<210> SEQ ID NO 19
<211> LENGTH: 1797
<212> TYPE: DNA
<213> ORGANISM: Oryza sativa

<400> SEQUENCE: 19
gcacgagggg agaagtatga ccctgatgga tcaacctggt acaattgggg cagtctcgct    60
tctcgcctcg tctcgtctcc ttcctccgac gcgcggaacc ttctagaagc ttctccctcc   120
ggtcggggga tgccgcgctg acccccctacc gtggttatgc tggcgtcaaa gctctggtcg   180
aggctcgcgt cgccgtcttc ccccgcctcg ccgcgcgccc tttcttcttc ttcatcggcg   240
gcggcggcgg cgaggtacct actgccgagc tctgggatgc cggcccaaga aggtcgccg   300 ggtcaccca gtgcggcga cgcgcggcc ggtgcgggc tcgggctcgc cgagactggg    360
tgtggcgcgg ccggtgcgcc gcgaccgctg ccgctgccgt gctcttcttc gtcggacaat   420
cccgcggaag agaatccttg cacaagacag atataccaaa gacagctaat gccgcatcgg   480
ttcaagttat ttttggggga gaaacgtcat tttacatatg caaatggtgc ttcactgaat   540
ccgcagaact acagatattt ttcatcttct tctggccaac agagtatagg aattggtaac   600
aagattatac atgaccttcc aagaagtgtg aaaattgtgg aagttgggcc acgagatggg   660
ctacagaatg agaagaacat agttccaaca catgtaaaga ttgaactcat acagagactg   720
gcaacctctg gattatcggt tgttgaggca actagttttg tctctccaaa atgggtacca   780
cagctagctg atgctaagga tgtgatggat gtagtccgga atattgaagg tgtaagcctt   840
cctgtattga caccaaacct taagggattt gaggcagctg ttgcagcagg tgcaaaagaa   900
gttgcagtat ttgcgtcagc ttctgaagca ttttccaagt caaacataaa ctgtaccatt   960
aaagagagcc ttgctcgcta taaagatgtt gctcttgcag caaaagagct aaaaatcccc  1020
atgcgagggt atgtttcttg tgtggttgga tgcccagtag aaggatatgt gccaccgtca  1080
aatgtagctc atgtggctaa agagctttat gacatgggct gctacgagt ttcacttggt  1140 gatacaatag gcgttggtac cccaggcacc gttgttccaa tgcttgaggc tgttatgttc  1200
tttgttccaa aggagaagct tgctgtccat ttccacgata cctacggcca atcgctttca  1260
aatatcctca tctctctcca gatgggtgtg agcgttgtgg actcttccgt agcgggcctc  1320
ggagggtgcc catacgcgaa aggtgcatcg ggcaatgtgc cgacgaggga cgtggtgtac  1380
atgctgaacg gctgggggat cagcaccaat gtcgacctgg caaggtgat ggccgccggc  1440
```

-continued

```
gagttcatct gcaaccatct ggggcgccag tctgggtcca aggcagctat cgctttggga   1500
agcaaggttg ctactgccaa cgcatccaaa ctgtgaggtt cactaacatt cactgatgca   1560
gtctttcgga ggatgcgttt cagacataca aatgtatacg ataaataaag gcgaaattgg   1620
ttccatgcta ttcaagtgac ctgggatttg tcggtgctag aaaactaaaa tcgggatcgt   1680
tgggtgatgt aagatcaatt ttgccagaaa taaatggact gatgggattg ttgattgata   1740
tatatggtca gcttttcctg aagaacttaa gctgaaaaaa aaaaaaaaaa aaaaaaa     1797
```

<210> SEQ ID NO 20
<211> LENGTH: 459
<212> TYPE: PRT
<213> ORGANISM: Oryza sativa

<400> SEQUENCE: 20

```
Met Leu Ala Ser Lys Leu Trp Ser Arg Leu Ala Ser Pro Ser Ser Pro
  1               5                  10                  15

Ala Ser Pro Arg Ala Leu Ser Ser Ser Ser Ala Ala Ala Ala Ala Ala
             20                  25                  30

Arg Tyr Leu Leu Pro Ser Ser Gly Met Pro Ala Gln Glu Arg Ser Pro
         35                  40                  45

Gly His Pro Ser Gly Gly Asp Ala Arg Pro Gly Ala Gly Leu Gly Leu
     50                  55                  60

Ala Glu Thr Gly Cys Gly Ala Ala Gly Ala Pro Arg Pro Leu Pro Leu
 65                  70                  75                  80

Pro Cys Ser Ser Ser Asp Asn Pro Ala Glu Glu Asn Pro Cys Thr
                 85                  90                  95

Arg Gln Ile Tyr Gln Arg Gln Leu Met Pro His Arg Phe Lys Leu Phe
            100                 105                 110

Leu Gly Glu Lys Arg His Phe Thr Tyr Ala Asn Gly Ala Ser Leu Asn
        115                 120                 125

Pro Gln Asn Tyr Arg Tyr Phe Ser Ser Ser Gly Gln Gln Ser Ile
    130                 135                 140

Gly Ile Gly Asn Lys Ile Ile His Asp Leu Pro Arg Ser Val Lys Ile
145                 150                 155                 160

Val Glu Val Gly Pro Arg Asp Gly Leu Gln Asn Glu Lys Asn Ile Val
                165                 170                 175

Pro Thr His Val Lys Ile Glu Leu Ile Gln Arg Leu Ala Thr Ser Gly
            180                 185                 190

Leu Ser Val Val Glu Ala Thr Ser Phe Val Ser Pro Lys Trp Val Pro
        195                 200                 205

Gln Leu Ala Asp Ala Lys Asp Val Met Asp Val Val Arg Asn Ile Glu
    210                 215                 220

Gly Val Ser Leu Pro Val Leu Thr Pro Asn Leu Lys Gly Phe Glu Ala
225                 230                 235                 240

Ala Val Ala Ala Gly Ala Lys Glu Val Ala Val Phe Ala Ser Ala Ser
                245                 250                 255

Glu Ala Phe Ser Lys Ser Asn Ile Asn Cys Thr Ile Lys Glu Ser Leu
            260                 265                 270

Ala Arg Tyr Lys Asp Val Ala Leu Ala Lys Glu Leu Lys Ile Pro
        275                 280                 285

Met Arg Gly Tyr Val Ser Cys Val Val Gly Cys Pro Val Glu Gly Tyr
    290                 295                 300

Val Pro Pro Ser Asn Val Ala His Val Ala Lys Glu Leu Tyr Asp Met
```

-continued

```
                305                 310                 315                 320
Gly Cys Tyr Glu Val Ser Leu Gly Asp Thr Ile Gly Val Gly Thr Pro
                    325                 330                 335
Gly Thr Val Val Pro Met Leu Glu Ala Val Met Phe Phe Val Pro Lys
                340                 345                 350
Glu Lys Leu Ala Val His Phe His Asp Thr Tyr Gly Gln Ser Leu Ser
            355                 360                 365
Asn Ile Leu Ile Ser Leu Gln Met Gly Val Ser Val Val Asp Ser Ser
        370                 375                 380
Val Ala Gly Leu Gly Gly Cys Pro Tyr Ala Lys Gly Ala Ser Gly Asn
385                 390                 395                 400
Val Ala Thr Glu Asp Val Val Tyr Met Leu Asn Gly Leu Gly Ile Ser
                405                 410                 415
Thr Asn Val Asp Leu Gly Lys Val Met Ala Ala Gly Glu Phe Ile Cys
                420                 425                 430
Asn His Leu Gly Arg Gln Ser Gly Ser Lys Ala Ala Ile Ala Leu Gly
            435                 440                 445
Ser Lys Val Ala Thr Ala Asn Ala Ser Lys Leu
    450                 455
```

<210> SEQ ID NO 21
<211> LENGTH: 1119
<212> TYPE: DNA
<213> ORGANISM: Glycine max

<400> SEQUENCE: 21

```
gcacgagaat aacaaaaatg tacaggatat gccatataag tttatgaaag gtataccaaa     60
atttgtaaag atagttgaag ttggtccaag ggatggatta caaaatgaga aaaacattgt    120
accaacagat gtaaagattg aattgattca tagattggca tcttctgggt tatccgtcat    180
tgaagctact agttttgtat ctcctaaatg ggtccctcag ttggcagatg caaaggatgt    240
aatgcaagca gttcataacc tgggaggcat tagattgcca gttctgactc ctaatttaaa    300
gggttttgaa gctgctatag cggctggtgc gagagaagta gctgttttg catcagcttc    360
tgaatctttc tcaaaatcaa acattaattg tagtattgaa gagagccttg tccgctatcg    420
agctgttact catgcggcta agagctctc tattcctgtt cgagggtatg tatcatgcgt    480
tgttggatgc ccgtggaag gaccaatccc tccgtcaaga gtggcatatg tagctaaaga    540
actatatgat atgggttgct tgaaatctc actcgggac acaattggag ttggtactcc    600
cggaactgta gttccaatgc ttttggctgt aatggctgtt gtgccagcgg agaagcttgc    660
tgtccacttc catgacactt acgggcaatc ccttgcaaat attcttgtgt cccttcaaat    720
ggggatcagt gcagttgatt cttcagttgc tggtctaggt ggctgtccat atgctaaggg    780
agcttcagga aatgtagcta ccgaagatgt tgtgtacatg ctgaatggac ttggtgtgaa    840
gaccaacgtt gatctcggaa agctcatgtc agctggtgag ttcatcggca agcatttggg    900
gcgcccatcc ggctcaaaga ctaccattgc ctttagccga gtaactgctg atgcttccaa    960
gatatgataa tatgttctac cgtaaaaaaa ttatatttgg atgctttaag caatgagagg   1020
acaccatatg tttcatcttt tttaccccat aattattgac aaagaataaa atgcccactc   1080
tcgttgatta gttgtgaagg aagaagtaat gcatgtttt                          1119
```

<210> SEQ ID NO 22
<211> LENGTH: 310
<212> TYPE: PRT

<213> ORGANISM: Glycine max

<400> SEQUENCE: 22

His Glu Asn Asn Lys Asn Val Gln Asp Met Pro Tyr Lys Phe Met Lys
1               5                   10                  15

Gly Ile Pro Lys Phe Val Lys Ile Val Glu Val Gly Pro Arg Asp Gly
            20                  25                  30

Leu Gln Asn Glu Lys Asn Ile Val Pro Thr Asp Val Lys Ile Glu Leu
        35                  40                  45

Ile His Arg Leu Ala Ser Ser Gly Leu Ser Val Ile Glu Ala Thr Ser
    50                  55                  60

Phe Val Ser Pro Lys Trp Val Pro Gln Leu Ala Asp Ala Lys Asp Val
65                  70                  75                  80

Met Gln Ala Val His Asn Leu Gly Ile Arg Leu Pro Val Leu Thr
                85                  90                  95

Pro Asn Leu Lys Gly Phe Glu Ala Ala Ile Ala Ala Gly Ala Arg Glu
                100                 105                 110

Val Ala Val Phe Ala Ser Ala Ser Glu Ser Phe Ser Lys Ser Asn Ile
            115                 120                 125

Asn Cys Ser Ile Glu Glu Ser Leu Val Arg Tyr Arg Ala Val Thr His
130                 135                 140

Ala Ala Lys Glu Leu Ser Ile Pro Val Arg Gly Tyr Val Ser Cys Val
145                 150                 155                 160

Val Gly Cys Pro Val Glu Gly Pro Ile Pro Ser Arg Val Ala Tyr
                165                 170                 175

Val Ala Lys Glu Leu Tyr Asp Met Gly Cys Phe Glu Ile Ser Leu Gly
            180                 185                 190

Asp Thr Ile Gly Val Gly Thr Pro Gly Thr Val Val Pro Met Leu Leu
        195                 200                 205

Ala Val Met Ala Val Val Pro Ala Glu Lys Leu Ala Val His Phe His
    210                 215                 220

Asp Thr Tyr Gly Gln Ser Leu Ala Asn Ile Leu Val Ser Leu Gln Met
225                 230                 235                 240

Gly Ile Ser Ala Val Asp Ser Ser Val Ala Gly Leu Gly Gly Cys Pro
                245                 250                 255

Tyr Ala Lys Gly Ala Ser Gly Asn Val Ala Thr Glu Asp Val Val Tyr
                260                 265                 270

Met Leu Asn Gly Leu Gly Val Lys Thr Asn Val Asp Leu Gly Lys Leu
            275                 280                 285

Met Ser Ala Gly Glu Phe Ile Gly Lys His Leu Gly Arg Pro Ser Gly
        290                 295                 300

Ser Lys Thr Thr Ile Ala
305                 310

<210> SEQ ID NO 23
<211> LENGTH: 1386
<212> TYPE: DNA
<213> ORGANISM: Glycine max

<400> SEQUENCE: 23
gcacgagaaa ttacaaacac aagagaagtt aagaatgact ttgacaaata ccatgtaaag     60
ggtttatctc gatgcctgaa ctggacttca aggtcaaatg ccaatagtca agcatcctgc    120
tatgtggtaa atcgtcattt tgcatctgat tgcaatgata tatgctcaaa ggagttctca    180
agtaagcttc ttacaagtat tccagactat gtaaagatag tggaagttgg tgcaagggat    240

```
ggattgcaaa atgagaaggc cattattcct actaatgtaa aagttgagtt aataaaactg    300
ctagtttctt ctgggttgtc agttgttgag gcgacaagtt ttgtctcacc aaaatgggta    360
ccccagttgg cagatgcaaa ggatgtactg gcagcaattc aaaatgttga aggtgctagg    420
tttcctgtct tgactccaaa ccttaaaggc tttgaggcag ctgttgctgc tggagctaaa    480
gaagtggctg tttttcctgc agcttctgaa tcattctcaa aagcaaatct gaattctagc    540
attgaggata tcttgctcg ttgccacgat attgcttcag ctgctagaag cctctcgatc    600
ccagttcgtg gatatatatc atgtgttgtc ggatgtcctc tggaaggaaa tattgctcca    660
gcaaaagttg catatgtggc aaaatcgctt tatgagatgg gttgctcaga gatttcactg    720
ggggatacaa tcggtgttgg cacacctggt actgtcattt caatgcttga agctgttctt    780
gatgttgttc caactgacat gcttgctgtc cactttcatg atacttatgg tcaggcactt    840
tcaaatattt taatttcact tcagatgggg atcagcacag tggattcatc tgtttctggt    900
cttggaggtt gtccatatgc caagggtgca actgggaatg tagccactga ggatgtcgtt    960
tacatgctga atggacttgg agtgaaaaca aatgtggacc ttggaaagct tatgcttgct   1020
ggggatttca tctgcaagca tttaggacgt gcatctggtt caaaagcagc tactgctttg   1080
agtaaagtta caagtcatgc ctccaaacta taagttacta tagctagtca tgcacctgca   1140
tgataggcac attgtttggc cactgtagaa tatgtattta tgttggtgtt tactgtcccg   1200
tgggccctgc ctatagaaaa gagagagcca gcaaacacaa ttgtaatgct gttcacttct   1260
gcttgtgttc tgagtcagtt tagtcgcttt gattattgag aaaaatcaca tgttgaacat   1320
gtactccgga acacacttat aaaattgcat agaatgtcca agttcaacaa aaaaaaaaa   1380 aaaaaa                                                               1386
```

<210> SEQ ID NO 24
<211> LENGTH: 370
<212> TYPE: PRT
<213> ORGANISM: Glycine max

<400> SEQUENCE: 24

```
Ala Arg Glu Ile Thr Asn Thr Arg Glu Val Lys Asn Asp Phe Asp Lys
  1               5                  10                  15

Tyr His Val Lys Gly Leu Ser Arg Cys Leu Asn Trp Thr Ser Arg Ser
             20                  25                  30

Asn Ala Asn Ser Gln Ala Ser Cys Tyr Val Val Asn Arg His Phe Ala
         35                  40                  45

Ser Asp Cys Asn Asp Ile Cys Ser Lys Glu Phe Ser Ser Lys Leu Leu
     50                  55                  60

Thr Ser Ile Pro Asp Tyr Val Lys Ile Val Glu Val Gly Ala Arg Asp
 65                  70                  75                  80

Gly Leu Gln Asn Glu Lys Ala Ile Ile Pro Thr Asn Val Lys Val Glu
                 85                  90                  95

Leu Ile Lys Leu Leu Val Ser Ser Gly Leu Ser Val Val Glu Ala Thr
            100                 105                 110

Ser Phe Val Ser Pro Lys Trp Val Pro Gln Leu Ala Asp Ala Lys Asp
        115                 120                 125

Val Leu Ala Ala Ile Gln Asn Val Glu Gly Ala Arg Phe Pro Val Leu
    130                 135                 140

Thr Pro Asn Leu Lys Gly Phe Glu Ala Ala Val Ala Ala Gly Ala Lys
145                 150                 155                 160
```

```
Glu Val Ala Val Phe Pro Ala Ala Ser Glu Ser Phe Ser Lys Ala Asn
                165                 170                 175

Leu Asn Ser Ser Ile Glu Asp Asn Leu Ala Arg Cys His Asp Ile Ala
            180                 185                 190

Ser Ala Ala Arg Ser Leu Ser Ile Pro Val Arg Gly Tyr Ile Ser Cys
            195                 200                 205

Val Val Gly Cys Pro Leu Glu Gly Asn Ile Ala Pro Lys Val Ala
        210                 215                 220

Tyr Val Ala Lys Ser Leu Tyr Glu Met Gly Cys Ser Glu Ile Ser Leu
225                 230                 235                 240

Gly Asp Thr Ile Gly Val Gly Thr Pro Gly Thr Val Ile Ser Met Leu
            245                 250                 255

Glu Ala Val Leu Asp Val Val Pro Thr Asp Met Leu Ala Val His Phe
            260                 265                 270

His Asp Thr Tyr Gly Gln Ala Leu Ser Asn Ile Leu Ile Ser Leu Gln
            275                 280                 285

Met Gly Ile Ser Thr Val Asp Ser Ser Val Ser Gly Leu Gly Gly Cys
        290                 295                 300

Pro Tyr Ala Lys Gly Ala Thr Gly Asn Val Ala Thr Glu Asp Val Val
305                 310                 315                 320

Tyr Met Leu Asn Gly Leu Gly Val Lys Thr Asn Val Asp Leu Gly Lys
            325                 330                 335

Leu Met Leu Ala Gly Asp Phe Ile Cys Lys His Leu Gly Arg Ala Ser
            340                 345                 350

Gly Ser Lys Ala Ala Thr Ala Leu Ser Lys Val Thr Ser His Ala Ser
            355                 360                 365

Lys Leu
    370

<210> SEQ ID NO 25
<211> LENGTH: 911
<212> TYPE: DNA
<213> ORGANISM: Triticum aestivum

<400> SEQUENCE: 25
gcacgagagg atcagtacca ccttcaaatg tagcttatgt tgccaaagag ctttatgaca      60
tgggctgcta cgaggtttcg cttggtgata cgattggagt tggtacccca ggcacagttg     120
taccaatgct tgaggcagtt atgtccgtcg ttcccgtgga aaagcttgct gtccatttcc     180
acgacaccta cggcagtctc ttttcaaaca tcctcgtctc tctccagatg ggtattagtg     240
tcgtggactc ctccgtcgca ggccttggtg gctgcccata tgcgcagggc gcatcaggga     300
atgttgctac tgaagacgta gtgtacatgc tgaatgggtt ggggatcaag acaggcgtcg     360
atctaagcaa ggtaatcgca gccggcgagt tcatctgcaa gcatctgggg cgccagtctg     420
ggtccaaggc agctactgcc ttgagcaagg ttaccgcgag cgcctcaaag ctatgaggtt     480
gctcttagtg ctgttactct gtaacatcat aatgctgtgc ccgtttattg tatgtcgtga     540 tccccctgttg cagaagatac atgtacagta ccaatgcaga aagtacgtaa atgaataaat     600
ggtgcatttt gctaaacata tcttgtacag gtttagcgtg tcccttttgta acacgctatg     660 aggccggcct tgaggctcac ggcagggtag ttaggaggtt tattcttttt atgttttatc     720
tctcttatct cctaaaccct cctgtaatat ctccgatgg ttagcttga cgctgccatc       780 tcctgtaccg actcccacaa tcaatatata ctccgcgggt ctccatgtat ggagattgag     840
acgcttaacc aaaaaaaaaa aaaaaaaaaa aaaaaaaaaa aaaatacttc gagggggggg     900
```
cgtaccaaat c                                                                911

<210> SEQ ID NO 26
<211> LENGTH: 157
<212> TYPE: PRT
<213> ORGANISM: Triticum aestivum

<400> SEQUENCE: 26

Thr Arg Gly Ser Val Pro Pro Ser Asn Val Ala Tyr Val Ala Lys Glu
  1               5                  10                  15

Leu Tyr Asp Met Gly Cys Tyr Glu Val Ser Leu Gly Asp Thr Ile Gly
                 20                  25                  30

Val Gly Thr Pro Gly Thr Val Val Pro Met Leu Glu Ala Val Met Ser
             35                  40                  45

Val Val Pro Val Glu Lys Leu Ala Val His Phe His Asp Thr Tyr Gly
         50                  55                  60

Gln Ser Leu Ser Asn Ile Leu Val Ser Leu Gln Met Gly Ile Ser Val
 65                  70                  75                  80

Val Asp Ser Ser Val Ala Gly Leu Gly Gly Cys Pro Tyr Ala Gln Gly
                 85                  90                  95

Ala Ser Gly Asn Val Ala Thr Glu Asp Val Val Tyr Met Leu Asn Gly
            100                 105                 110

Leu Gly Ile Lys Thr Gly Val Asp Leu Ser Lys Val Ile Ala Ala Gly
        115                 120                 125

Glu Phe Ile Cys Lys His Leu Gly Arg Gln Ser Gly Ser Lys Ala Ala
130                 135                 140

Thr Ala Leu Ser Lys Val Thr Ser Ala Ser Lys Leu
145                 150                 155

<210> SEQ ID NO 27
<211> LENGTH: 1056
<212> TYPE: DNA
<213> ORGANISM: Zea mays

<400> SEQUENCE: 27
gcacgaggct gatcagtggg gagcatatcg gggcactggc gatgagtgaa cccaactctg    60
gctctgatgt cgtcagcatg aagtgcaaag ctgagaaagt ggacggtggc tatgtcctta   120
atgggaataa gatgtggtgc accaatggcc cgtctgctca gacactggtt gtttacgcaa   180
aaacagatct agctgcaggg tcaaaaggaa taactgcatt cataatcgag aaagggatgc   240
ccgggttcag tactgctcag aagttggaca aacttggcat gagaggaagc gacacgtgtg   300
agcttgtttt tgagaactgc tttgtgccat gcgaaaatgt cctcggtgaa gaaggcaaag   360
gtgtttatgt catgatgtca gggcttgatc tggaaaggct tgtattagct gcgggcccta   420
ttggccttat gcaggcatgc cttgatgttg tacttccata tgttcgccag agggagcaat   480
tcgcccgtcc atttgttgaa tttcagttca tacagggaa aatggctgat atgtacactt   540
cgttgcagtc gtcaagatca tttgtgtact cagttgctag ggactgcgat aatgcaaag   600
ttgatcgcaa ggattgtgca ggagtaattc tctttgctgc tgaaaatgca cccaagttg   660
cacttcaggc aatccagtgt cttggtggaa atgggtacat aaatgagtac ccaactggtc   720
gtctcctgag agatgcaaaa ttgtttgaga ttggtgccgg tactagtgag gtaagaagaa   780
tgataattgg ccgtgagctc ttcaaagagg actgaaactt ctattttgca agccagatat   840
cagagcatat tgttagctgg aggaggtgag ggcgatttag atatttagca aatcaccct    900

-continued

```
gtggttcaat gcttttgtat aaccgcagac atacatcaaa taaagttcac ttgtacttgc      960
tgcttgcagt ggctctattt ttctgtcaat aaagtttttt atgtctctga cttaaaaaaa     1020
aaaaaaaata aatactcga gggcgggccc aaccat                                1056
```

```
<210> SEQ ID NO 28
<211> LENGTH: 270
<212> TYPE: PRT
<213> ORGANISM: Zea mays

<400> SEQUENCE: 28
```

```
Thr Arg Leu Ile Ser Gly Glu His Ile Gly Ala Leu Ala Met Ser Glu
 1               5                  10                  15

Pro Asn Ser Gly Ser Asp Val Val Ser Met Lys Cys Lys Ala Glu Lys
            20                  25                  30

Val Asp Gly Gly Tyr Val Leu Asn Gly Asn Lys Met Trp Cys Thr Asn
        35                  40                  45

Gly Pro Ser Ala Gln Thr Leu Val Val Tyr Ala Lys Thr Asp Leu Ala
    50                  55                  60

Ala Gly Ser Lys Gly Ile Thr Ala Phe Ile Ile Glu Lys Gly Met Pro
65                  70                  75                  80

Gly Phe Ser Thr Ala Gln Lys Leu Asp Lys Leu Gly Met Arg Gly Ser
                85                  90                  95

Asp Thr Cys Glu Leu Val Phe Glu Asn Cys Phe Val Pro Cys Glu Asn
            100                 105                 110

Val Leu Gly Glu Glu Gly Lys Gly Val Tyr Val Met Met Ser Gly Leu
        115                 120                 125

Asp Leu Glu Arg Leu Val Leu Ala Ala Gly Pro Ile Gly Leu Met Gln
    130                 135                 140

Ala Cys Leu Asp Val Val Leu Pro Tyr Val Arg Gln Arg Glu Gln Phe
145                 150                 155                 160

Ala Arg Pro Phe Val Glu Phe Gln Phe Ile Gln Gly Lys Met Ala Asp
                165                 170                 175

Met Tyr Thr Ser Leu Gln Ser Ser Arg Ser Phe Val Tyr Ser Val Ala
            180                 185                 190

Arg Asp Cys Asp Asn Gly Lys Val Asp Arg Lys Asp Cys Ala Gly Val
        195                 200                 205

Ile Leu Phe Ala Ala Glu Asn Ala Thr Gln Val Ala Leu Gln Ala Ile
    210                 215                 220

Gln Cys Leu Gly Gly Asn Gly Tyr Ile Asn Glu Tyr Pro Thr Gly Arg
225                 230                 235                 240

Leu Leu Arg Asp Ala Lys Leu Phe Glu Ile Gly Ala Gly Thr Ser Glu
                245                 250                 255

Val Arg Arg Met Ile Ile Gly Arg Glu Leu Phe Lys Glu Asp
            260                 265                 270
```

```
<210> SEQ ID NO 29
<211> LENGTH: 1539
<212> TYPE: DNA
<213> ORGANISM: Oryza sativa

<400> SEQUENCE: 29
```

```
gcacgaggtt taaacagacg gcgacggatt gcgcgggcgc aagcagcact caagttcgct       60
agtcctcctc ctccttcctg tgtagtggag cgaggcgagg cgagccgacg ccatggccgc      120
ggcgcagcgc tggctcccotg ggatcctccg ccgaggggac gggctcgcgc ggcgcctcta     180
```

-continued

```
ctcctccgcc tcctccctcc tcttcgacga cacccaggag cagttcaagg agagcgtgca      240
caagttcgcg caggagacca tcgccccgca cgccgccgcc atcgacgcct ccaaccattt      300
ccccaaggac gtcaacctct ggaagctcat gggcgatttc aatctccacg gcctcaccgc      360
cccagaagag tatggtggga tggggctcgg ctacatgtac cactgcattg ccatggagga      420
gatcaacagg gcgtccggct cggtcggcct gtcttacagc gctcactcca acctctgcat      480
taaccaactg gtccggcatg gcagccctgc ccaaaagctc aagtacttac aaagctaat       540 cactggggag catgtggggg cattggcgat gagcgaaccc aactctgggt ctgatgttgt      600
cagtatgaag tgcaaagctg agaaagtata tggtgggtat gtcattaacg ggaataagat      660
gtggtgcacc aacgggccat ctgctcagac actgggtgtg tatgcaaaaa cagatataac      720
tgctggatca aaaggaataa ccgcgttcat aattgagaag gggatggccg ggttcagtac      780
tgcacagaag ttggacaagc ttggcatgag aggaagtgac acatgtgagc ttgtgttcga      840
gaattgtttt gtcccccatg aaaacgttct cggggaagaa gggaaaggtg tttatgtcat      900
gatgtcaggg cttaatctag aaagatttgt gttagctgca ggtcctagcg ccctcatgca      960
agcatgcctt gatgtagctg ttctttatgt tcgccaaaga gagcaatttg gccgcccaat     1020
tggtgaattt cagttcatac gggggaaatt ggcagatatg tacacctcct tgcagtcatc     1080
aaggtcattt gtttactcgg ttgctaggga ctgtgacaat ggtaaagttg accgcaagga     1140
ttgtgctggt gtgattctct ttgctgctga agggcaacc caggttgcac ttcaggcaat      1200
acagtgtctt ggtggcaacg gatacataaa tgagtaccca actgcccgat gctgagaga     1260 tgcaaaactg tttgagattg gacccggtac tagtgagata agaagaatga taattgcccg     1320
cgagctcttc aaagaggagt gaaactatta ttttggaagc caggtatctg atatgtataa     1380
cttggggagg tgagcatgat ttggacaatt tgtacacatc gtccctgatg tcctatatct     1440
gataatttgt ccaagatttg tcatgacttt gtatatttcc aatttaataa gaaataaaat     1500
gcacctttct ttaaaaaaaa aaaaaaaaa aaaaaaaaa                              1539
```

<210> SEQ ID NO 30
<211> LENGTH: 409
<212> TYPE: PRT
<213> ORGANISM: Oryza sativa

<400> SEQUENCE: 30

```
Met Ala Ala Ala Gln Arg Trp Leu Pro Gly Ile Leu Arg Arg Gly Asp
  1               5                  10                  15

Gly Leu Ala Arg Arg Leu Tyr Ser Ser Ala Ser Ser Leu Leu Phe Asp
                 20                  25                  30

Asp Thr Gln Glu Gln Phe Lys Glu Ser Val His Lys Phe Ala Gln Glu
             35                  40                  45

Thr Ile Ala Pro His Ala Ala Ala Ile Asp Ala Ser Asn His Phe Pro
         50                  55                  60

Lys Asp Val Asn Leu Trp Lys Leu Met Gly Asp Phe Asn Leu His Gly
 65                  70                  75                  80

Leu Thr Ala Pro Glu Glu Tyr Gly Gly Met Gly Leu Gly Tyr Met Tyr
                 85                  90                  95

His Cys Ile Ala Met Glu Glu Ile Asn Arg Ala Ser Gly Ser Val Gly
                100                 105                 110

Leu Ser Tyr Ser Ala His Ser Asn Leu Cys Ile Asn Gln Leu Val Arg
            115                 120                 125

His Gly Ser Pro Ala Gln Lys Leu Lys Tyr Leu Pro Lys Leu Ile Thr
```

```
              130                 135                 140
Gly Glu His Val Gly Ala Leu Ala Met Ser Glu Pro Asn Ser Gly Ser
145                 150                 155                 160

Asp Val Val Ser Met Lys Cys Lys Ala Glu Lys Val Tyr Gly Gly Tyr
                165                 170                 175

Val Ile Asn Gly Asn Lys Met Trp Cys Thr Asn Gly Pro Ser Ala Gln
                180                 185                 190

Thr Leu Gly Val Tyr Ala Lys Thr Asp Ile Thr Ala Gly Ser Lys Gly
                195                 200                 205

Ile Thr Ala Phe Ile Ile Glu Lys Gly Met Ala Gly Phe Ser Thr Ala
                210                 215                 220

Gln Lys Leu Asp Lys Leu Gly Met Arg Gly Ser Asp Thr Cys Glu Leu
225                 230                 235                 240

Val Phe Glu Asn Cys Phe Val Pro His Glu Asn Val Leu Gly Glu Glu
                245                 250                 255

Gly Lys Gly Val Tyr Val Met Met Ser Gly Leu Asn Leu Glu Arg Phe
                260                 265                 270

Val Leu Ala Ala Gly Pro Ser Ala Leu Met Gln Ala Cys Leu Asp Val
                275                 280                 285

Ala Val Leu Tyr Val Arg Gln Arg Glu Gln Phe Gly Arg Pro Ile Gly
                290                 295                 300

Glu Phe Gln Phe Ile Arg Gly Lys Leu Ala Asp Met Tyr Thr Ser Leu
305                 310                 315                 320

Gln Ser Ser Arg Ser Phe Val Tyr Ser Val Ala Arg Asp Cys Asp Asn
                325                 330                 335

Gly Lys Val Asp Arg Lys Asp Cys Ala Gly Val Ile Leu Phe Ala Ala
                340                 345                 350

Glu Arg Ala Thr Gln Val Ala Leu Gln Ala Ile Gln Cys Leu Gly Gly
                355                 360                 365

Asn Gly Tyr Ile Asn Glu Tyr Pro Thr Ala Arg Leu Leu Arg Asp Ala
370                 375                 380

Lys Leu Phe Glu Ile Gly Pro Gly Thr Ser Glu Ile Arg Arg Met Ile
385                 390                 395                 400

Ile Ala Arg Glu Leu Phe Lys Glu Glu
                405

<210> SEQ ID NO 31
<211> LENGTH: 1553
<212> TYPE: DNA
<213> ORGANISM: Glycine max

<400> SEQUENCE: 31
gcacgaggat caattttcaa ttttcaattg tgcccatctt cgttgctgcc accatgcata      60
ggatcaacac cgcaaggccc attttttctg ctgttttcag aagcaaatct cggcctcact     120
ctgctgcttt ctccacctcc ttgctcttcg acgaaactca gacacagttt aaggaaagtg     180
ttgctcaatt tgcaacggaa atattgccc tcatgcttc gaaatagac caaacaaatt       240
atttcccaaa ggaggtgaac ttatggaaaa gcatggggga atttaatctc cttgggatta     300
ctgcaccaga ggaatatgga gggcttggcc taggttactt gtatcactgt atagcaatgg     360
aagagattag ccgtgcttca ggatctgtag gtctttctta tggtgctcat tcaaacttgt     420
gtatcaatca gctggtgagg aatggaagcc ctgctcagaa agagaaatat ttaccaaagc     480
ttatttctgg ggatcatgtg ggagctttgg caatgagcga gcccaattct ggttctgatg     540
```

-continued

| | |
|---|---|
| ttgtcagcat gaaatgcaag gctgatcgtg tagatggggg ctatgtactt aatgggaaca | 600 |
| agatgtggtg tactaatggg ccagttgctc aaacattagt tgtctatgct aaaacagaca | 660 |
| taactgctgg gtcaaaaggc attactgcat tcatcattga gaagggaatg cctggattca | 720 |
| atactgccca gaaattggat aaacttggga tgcgaggaag tgatacgtgt gagcttgtct | 780 |
| ttgagaattg ctttgttcca gacgaaaata ttcttgggaa agaagggaaa ggagtctatg | 840 |
| tcatgatgtc tgggctggat ctggagagac ttgttttggc agctggtcct cttggtatta | 900 |
| tgcaggcatg tcttgatgtc gtccttcctt atgttcgaca acgagagcag tttggtcgtc | 960 |
| ctattgggga gtttcagttt atacagggga aaattgctga catgtatact tcattacagt | 1020 |
| cttctaggtc ttatgtgtat tcagtagctc gggattgtga caacggaaaa gttgacccaa | 1080 |
| aggattgtgc tggagctata ctttgtgcag ctgaaagagc aacccaggtt gctttgcagg | 1140 |
| caatacaatg tttaggtggg aatggttatg tgaatgagta tcctactggt cgtctcttga | 1200 |
| gagatgccaa actctacgag attggtgcag gaactagtga gatcagaaga atgattattg | 1260 |
| gacgtgaact cttcaaggag caatacatgc caccatacct tatatgtgga tggtgttgag | 1320 |
| cccccttggga aattcccttg cagatgtttg ttaaactaat gctacattca tcaaacgaga | 1380 |
| attgatcatt ggtccaagga ataaaattct gccatattac attttttatat actttgaaaa | 1440 |
| tcttcaaagc gatcatccat cttagaaaac aatgttgtaa aactatcaac agcagttgac | 1500 |
| acagataata ataacttaag tatcttaatc aaataaaaaa aaaaaaaaaa aaa | 1553 |

<210> SEQ ID NO 32
<211> LENGTH: 427
<212> TYPE: PRT
<213> ORGANISM: Glycine max

<400> SEQUENCE: 32

Thr Arg Ile Asn Phe Gln Phe Ser Ile Val Pro Ile Phe Val Ala Ala
 1               5                  10                  15

Thr Met His Arg Ile Asn Thr Ala Arg Pro Ile Phe Ser Ala Val Phe
             20                  25                  30

Arg Ser Lys Ser Arg Pro His Ser Ala Ala Phe Ser Thr Ser Leu Leu
         35                  40                  45

Phe Asp Glu Thr Gln Thr Gln Phe Lys Glu Ser Val Ala Gln Phe Ala
     50                  55                  60

Thr Glu Asn Ile Ala Pro His Ala Ser Lys Ile Asp Gln Thr Asn Tyr
 65                  70                  75                  80

Phe Pro Lys Glu Val Asn Leu Trp Lys Ser Met Gly Glu Phe Asn Leu
                 85                  90                  95

Leu Gly Ile Thr Ala Pro Glu Glu Tyr Gly Gly Leu Gly Leu Gly Tyr
            100                 105                 110

Leu Tyr His Cys Ile Ala Met Glu Glu Ile Ser Arg Ala Ser Gly Ser
        115                 120                 125

Val Gly Leu Ser Tyr Gly Ala His Ser Asn Leu Cys Ile Asn Gln Leu
    130                 135                 140

Val Arg Asn Gly Ser Pro Ala Gln Lys Glu Lys Tyr Leu Pro Lys Leu
145                 150                 155                 160

Ile Ser Gly Asp His Val Gly Ala Leu Ala Met Ser Glu Pro Asn Ser
                165                 170                 175

Gly Ser Asp Val Val Ser Met Lys Cys Lys Ala Asp Arg Val Asp Gly
            180                 185                 190

Gly Tyr Val Leu Asn Gly Asn Lys Met Trp Cys Thr Asn Gly Pro Val

```
                    195                 200                 205
Ala Gln Thr Leu Val Val Tyr Ala Lys Thr Asp Ile Thr Ala Gly Ser
    210                 215                 220

Lys Gly Ile Thr Ala Phe Ile Ile Glu Lys Gly Met Pro Gly Phe Asn
225                 230                 235                 240

Thr Ala Gln Lys Leu Asp Lys Leu Gly Met Arg Gly Ser Asp Thr Cys
                245                 250                 255

Glu Leu Val Phe Glu Asn Cys Phe Val Pro Asp Glu Asn Ile Leu Gly
            260                 265                 270

Lys Glu Gly Lys Gly Val Tyr Val Met Met Ser Gly Leu Asp Leu Glu
        275                 280                 285

Arg Leu Val Leu Ala Ala Gly Pro Leu Gly Ile Met Gln Ala Cys Leu
    290                 295                 300

Asp Val Val Leu Pro Tyr Val Arg Gln Arg Glu Gln Phe Gly Arg Pro
305                 310                 315                 320

Ile Gly Glu Phe Gln Phe Ile Gln Gly Lys Ile Ala Asp Met Tyr Thr
                325                 330                 335

Ser Leu Gln Ser Ser Arg Ser Tyr Val Tyr Ser Val Ala Arg Asp Cys
            340                 345                 350

Asp Asn Gly Lys Val Asp Pro Lys Asp Cys Ala Gly Ala Ile Leu Cys
        355                 360                 365

Ala Ala Glu Arg Ala Thr Gln Val Ala Leu Gln Ala Ile Gln Cys Leu
    370                 375                 380

Gly Gly Asn Gly Tyr Val Asn Glu Tyr Pro Thr Gly Arg Leu Leu Arg
385                 390                 395                 400

Asp Ala Lys Leu Tyr Glu Ile Gly Ala Gly Thr Ser Glu Ile Arg Arg
                405                 410                 415

Met Ile Ile Gly Arg Glu Leu Phe Lys Glu Gln
            420                 425
```

<210> SEQ ID NO 33
<211> LENGTH: 766
<212> TYPE: DNA
<213> ORGANISM: Triticum aestivum

<400> SEQUENCE: 33

```
caagcaagct tttgtactct gctccagtca tccgtcgtct cccttccgc cgagatgcag    60
cgccggctcc cggcgctcct ccgccgcgcg gcgggcgcgg ggcccgcgcg ccggtggctc   120
tccgcctcgt cctccctcct cttcgacgac acccaggagc agttcaagga gagcgtgcac   180
cggttcgcgc aggagcacat cgcgccgcac gccgccgcca tcgacgcctc caaccacttc   240
cccaaggaga gaatctgtg gaagctcatg ggggacttca acctgcacgg cctcacctcg   300
ccagaggagt acgagggct cgggctcggt tacatgcacc actgcatcgc catgcaggag   360
atcagcaggg cgtccgggtc ggtcggcctt tcctacggtg cacactcaaa tctctgcatc   420
aaccagctgg tccgtcatgg cagccctgcc caaaaggaaa agtatttgcc gaagcttatc   480
agtggggagc atattggggc attggcgatg agtgaaccaa actctggctc tgatgttgtc   540
agtatgaagt gcaaagctga gaaagtagat ggcggctatg tcattaacgg aacaagatg   600
tggtgcacaa atggtccgtc tgctcagaca ttggttgttt acgcgaaaac agatataact   660
gctggatcga aggaataac tgcattcata attgagaagg gaatgcccgg gttcagtact   720
gcccagaagt tggacaaact tggcatgcga ggaagtgacc tcgtgc              766
```

-continued

```
<210> SEQ ID NO 34
<211> LENGTH: 255
<212> TYPE: PRT
<213> ORGANISM: Triticum aestivum

<400> SEQUENCE: 34

Gln Ala Ser Phe Cys Thr Leu Leu Gln Ser Ser Val Val Ser Leu Ser
  1               5                  10                  15

Ala Glu Met Gln Arg Arg Leu Pro Ala Leu Leu Arg Arg Ala Ala Gly
             20                  25                  30

Ala Gly Pro Ala Arg Arg Trp Leu Ser Ala Ser Ser Ser Leu Leu Phe
         35                  40                  45

Asp Asp Thr Gln Glu Gln Phe Lys Glu Ser Val His Arg Phe Ala Gln
 50                  55                  60

Glu His Ile Ala Pro His Ala Ala Ile Asp Ala Ser Asn His Phe
 65                  70                  75                  80

Pro Lys Glu Lys Asn Leu Trp Lys Leu Met Gly Asp Phe Asn Leu His
                 85                  90                  95

Gly Leu Thr Ser Pro Glu Glu Tyr Gly Gly Leu Gly Leu Gly Tyr Met
                100                 105                 110

His His Cys Ile Ala Met Glu Glu Ile Ser Arg Ala Ser Gly Ser Val
            115                 120                 125

Gly Leu Ser Tyr Gly Ala His Ser Asn Leu Cys Ile Asn Gln Leu Val
        130                 135                 140

Arg His Gly Ser Pro Ala Gln Lys Glu Lys Tyr Leu Pro Lys Leu Ile
145                 150                 155                 160

Ser Gly Glu His Ile Gly Ala Leu Ala Met Ser Glu Pro Asn Ser Gly
                165                 170                 175

Ser Asp Val Val Ser Met Lys Cys Lys Ala Glu Lys Val Asp Gly Gly
            180                 185                 190

Tyr Val Ile Asn Gly Asn Lys Met Trp Cys Thr Asn Gly Pro Ser Ala
        195                 200                 205

Gln Thr Leu Val Val Tyr Ala Lys Thr Asp Ile Thr Ala Gly Ser Lys
    210                 215                 220

Gly Ile Thr Ala Phe Ile Ile Glu Lys Gly Met Pro Gly Phe Ser Thr
225                 230                 235                 240

Ala Gln Lys Leu Asp Lys Leu Gly Met Arg Gly Ser Asp Leu Val
                245                 250                 255
```

ENZYMES INVOLVED IN DEGRADATION OF BRANCHED-CHAIN AMINO ACIDS

This application claims priority benefit of U.S. Provisional Application No. 60/094,990 filed Jul. 31, 1998, now pending.

FIELD OF THE INVENTION

This invention is in the field of plant molecular biology. More specifically, this invention pertains to nucleic acid fragments encoding enzymes involved in degradation of branched-chain amino acids in plants and seeds.

BACKGROUND OF THE INVENTION

Amino acids, in addition to their role as protein monomeric units, are energy metabolites and precursors of many biologically important nitrogen-containing compounds, notably heme, physiologically active amines, glutathione, nucleotides, and nucleotide coenzymes. Excess dietary amino acids are neither stored for future use nor excreted. Rather they are converted to common metabolic intermediates such as pyruvate, oxaloacetate, and alpha-ketoglutarate. Consequently, amino acids are also precursors of glucose, fatty acids, and ketone bodies and are therefore metabolic fuels.

Hydroxymethylglutaryl-CoA lyase (EC 4.1.3.4), also called HMG-CoA lyase, is involved in the degradation of leucine, and participates in butanoate metabolism, and in the synthesis and degradation of ketone bodies. HMG-CoA lyase catalyzes the final step of ketogenesis and leucine catabolism in the mitochondrial matrix. The first reported HMG-CoA lyase gene was from *Pseudomonas mevalonii* (Anderson, D. H. and Rodwell, V. W. (1989) *J Bacteriol.* 171:6468–6472). The active site of the *Pseudomonas mevalonii* HMG-CoA lyase has been identified. Cys-237 is required for catalysis (Hruz, P. W. et al. (1992) *Biochemistry* 31:6842–6847). To date, HMG-CoA lyase has not been described in plants.

3-Hydroxyisobutyrate dehydrogenase (EC 1.1.1.31) catalyzes the NAD-dependent, reversible oxidation of 3-hydroxbutyrate to methylmalonate (Rougraff, P. M. et al. (1989) *J. Biol. Chem.* 264:5899–5903). In animals, it is a homodimeric mitochondrial protein involved in valine catabolism. In *Pseudomonas aeruginosa* (encoded by the mmsB), it is involved in the-distal valine metabolic pathway (Steele, M. I. et al. (1992) *J. Biol. Chem.* 267:13585–13592). The sequence of 3-hydroxyisobutyrate dehydrogenase from eukaryotic and prokaryotic sources show that this enzyme has been well conserved throughout evolution. The pathway of valine catabolism ultimately leads to the production of succinyl-SCoA. Succinyl-SCoA can be converted to pyruvate via the TCA cycle and then to glucose. Thus, this enzyme is needed, along with several others in the catabolic pathway, to interconvert the carbon skeleton of valine into other useful metabolites. 3-hydroxyiso-butyrate dehydrogenase has not been isolated from plants yet, although rice ESTs encoding portions of this gene are present in the GenBank database.

Involved in the processing of leucine, isovalyryl-CoA dehydrogenase (EC 1.3.99.10) uses FAD to convert isovalyryl-CoA to beta-methylcrotonyl-CoA. This enzyme is found in the mitochondria and has similarity with other acyl-CoA dehydrogenases (long chain acyl-CoA (LCAD), short chain acyl-CoA (SCAD), and medium-chain (MCAD) acyl-CoA dehydrogenases). The structural relatedness of these enzymes suggests that they are members of a gene family that shares a common ancestral gene (Matsubara et. al. (1989) *J Biol Chem* 264(27):16321–16331). Rice and oat ESTs exist in the GenBank database but the enzyme has not yet been isolated from plants.

SUMMARY OF THE INVENTION

The instant invention relates to isolated nucleic acid fragments encoding enzymes involved in degradation of branched-chain amino acids. Specifically, this invention concerns an isolated nucleic acid fragment encoding a hydroxymethylglutaryl CoA oxidase, a 3-hydroxyisobutyrate dehydrogenase or an isovalyryl-CoA dehydrogenase and an isolated nucleic acid fragment that is substantially similar to an isolated nucleic acid fragment encoding a hydroxymethylglutaryl CoA oxidase, a 3-hydroxyisobutyrate dehydrogenase or an isovalyryl-CoA dehydrogenase. In addition, this invention relates to a nucleic acid fragment that is complementary to the nucleic acid fragment encoding hydroxymethyl-glutaryl CoA oxidase, 3-hydroxyisobutyrate dehydrogenase or isovalyryl-CoA dehydrogenase.

An additional embodiment of the instant invention pertains to a polypeptide encoding all or a substantial portion of a branched-chain amino acid degradation enzyme selected from the group consisting of hydroxymethylglutaryl CoA oxidase, 3-hydroxyisobutyrate dehydrogenase or isovalyryl-CoA dehydrogenase.

In another embodiment, the instant invention relates to a chimeric gene encoding a hydroxymethylglutaryl CoA oxidase, a 3-hydroxyisobutyrate dehydrogenase, or an isovalyryl-CoA dehydrogenase, or to a chimeric gene that comprises a nucleic acid fragment that is complementary to a nucleic acid fragment encoding a hydroxymethylglutaryl CoA oxidase, a 3-hydroxyisobutyrate dehydrogenase, or an isovalyryl-CoA dehydrogenase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a hydroxymethylglutaryl CoA oxidase, a 3-hydroxyisobutyrate dehydrogenase, or an isovalyryl-CoA dehydrogenase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a hydroxymethylglutaryl CoA oxidase, a 3-hydroxyisobutyrate dehydrogenase, or an isovalyryl-CoA dehydrogenase in a transformed host cell comprising: a) transforming a host cell with a chimeric gene comprising a nucleic acid fragment encoding a hydroxymethylglutaryl CoA oxidase, a 3-hydroxyisobutyrate dehydrogenase, or an isovalyryl-CoA dehydrogenase; and b) growing the transformed host cell under conditions that are suitable for expression of the chimeric gene wherein expression of the chimeric gene results in production of altered levels of hydroxymethylglutaryl CoA oxidase, 3-hydroxyisobutyrate dehydrogenase or isovaleryl-CoA dehydrogenase in the transformed host cell.

An addition embodiment of the instant invention concerns a method for obtaining a nucleic acid fragment encoding all or a substantial portion of an amino acid sequence encoding a hydroxymethylglutaryl CoA oxidase, a 3-hydroxyisobutyrate dehydrogenase, or an isovaleryl-CoA dehydrogenase.

A further embodiment of the instant invention is a method for evaluating at least one compound for its ability to inhibit the activity of a hydroxymethylglutaryl CoA oxidase, a 3-hydroxyisobutyrate dehydrogenase, or an isovaleryl-CoA dehydrogenase, the method comprising the steps of: (a) transforming a host cell with a chimeric gene comprising a nucleic acid fragment encoding a hydroxymethylglutaryl CoA oxidase, a 3-hydroxyiso-butyrate dehydrogenase, or an isovaleryl-CoA dehydrogenase, operably linked to suitable regulatory sequences; (b) growing the transformed host cell under conditions that are suitable for expression of the chimeric gene wherein expression of the chimeric gene results in production of hydroxymethylglutaryl CoA oxidase, 3-hydroxyisobutyrate dehydrogenase or isovaleryl-CoA dehydrogenase in the transformed host cell; (c) optionally purifying the hydroxymethylglutaryl CoA oxidase, the 3-hydroxyisobutyrate dehydrogenase or the isovaleryl-CoA dehydrogenase expressed by the transformed host cell; (d) treating the hydroxymethylglutaryl CoA oxidase, the 3-hydroxyisobutyrate dehydrogenase or the isovaleryl-CoA dehydrogenase with a compound to be tested; and (e) comparing the activity of the hydroxymethylglutaryl CoA oxidase, the 3-hydroxyisobutyrate dehydrogenase or the isovaleryl-CoA dehydrogenase that has been treated with a test compound to the activity of an untreated hydroxymethylglutaryl CoA oxidase, 3-hydroxyisobutyrate dehydrogenase or isovaleryl-CoA dehydrogenase, thereby selecting compounds with potential for inhibitory activity.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Branched-Chain Amino Acid Degradation Enzymes

| Protein | Clone Designation | SEQ ID NO: (Nucleotide) | SEQ ID NO: (Amino Acid) |
|---|---|---|---|
| 3-Hydroxy-isobutyrate Dehydrogenase | Contig of: cen3n.pk0138.e1 cta1n.pk0052.d10 p0037.crwak74r | 1 | 2 |
| | Contig of: cr1n.pk0191.b10 p0076.cwhan08r | 3 | 4 |

TABLE 1-continued

Branched-Chain Amino Acid Degradation Enzymes

| Protein | Clone Designation | SEQ ID NO: (Nucleotide) | SEQ ID NO: (Amino Acid) |
|---|---|---|---|
| | p0118.chsbe01r rr1.pk0032.d4 | 5 | 6 |
| | ses2w.pk0002.e5 | 7 | 8 |
| | Contig of: sl2.pk0099.g8 src2c.pk020.g23 | 9 | 10 |
| | Contig of: wdk3c.pk005.g5 wlk1.pk0001.g3 wre1n.pk0014.c1 | 11 | 12 |
| Hydroxy-methylglutaryl-CoA Lyase | Contig of: cbn10.pk0004.g10 cbn10.pk0031.a5 cco1n.pk062.k1 cct1c.pk001.c19 csi1n.pk0050.f7 p0043.cimao89r p0044.cjrag28r p0072.comfk14r p0072.comft16r | 13 | 14 |
| | Contig of: cbn10.pk0039.e6 cen3n.pk0107.b6 p0031.ccmaw86r p0117.chcln34r | 15 | 16 |
| | rl0n.pk089.g16 | 17 | 18 |
| | rsl1n.pk006.j2 | 19 | 20 |
| | sdp3c.pk010.f19 | 21 | 22 |
| | sre.pk0032.d4 | 23 | 24 |
| | wl1n.pk0132.f6 | 25 | 26 |
| Isovaleryl-CoA Dehydrogenase | cbn10.pk0034.e3:fis | 27 | 28 |
| | rlr6.pk0079.d12:fis | 29 | 30 |
| | sr1.pk0107.d1 | 31 | 32 |
| | wlk4.pk0023.a11:fis | 33 | 34 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several branched-chain amino acid degradation enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other hydroxymethylglutaryl CoA oxidases, 3-hydroxyisobutyrate dehydrogenases or isovalyryl-CoA dehydrogenases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1: 165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of valine, leucine, or isoleucine in those cells. This may result in the accumulation of toxic compounds such as 3-hydroxyisobutyrate which would be a useful herbicide target.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded branched-chain amino acid degradation enzymes. An example of a vector for high level expression of the instant polypeptides in a bacterial host is provided (Example 8).

Additionally, the instant polypeptides can be used as targets to facilitate design and/or identification of inhibitors of those enzymes that may be useful as herbicides. This is desirable because the polypeptides described herein catalyze various steps in degradation of branched-chain amino acids. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) Plant Cell 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn10 | Corn Developing Kernel (Embryo and Endosperm); 10 Days After Pollination | cbn10.pk0004.g10 cbn10.pk0031.a5 cbn10.pk0034.e3 cbn10.pk0039.e6 |
| cco1n | Corn Cob of 67 Day Old Plants Grown in Green House* | cco1n.pk062.k1 |
| cct1c | Corn Callus Tissue Transformed With Construct 11870 | cct1c.pk001.c19 |
| cen3n | Corn Endosperm 20 Days After Pollination* | cen3n.pk0107.b6 cen3n.pk0138.e1 |
| cr1n | Corn Root From 7 Day Old Seedlings* | cr1n.pk0191.b10 |
| csi1n | Corn Silk* | csi1n.pk0050.f7 |
| cta1n | Corn Tassel* | cta1n.pk0052.d10 |
| p0031 | Corn Shoot Culture | p0031.ccmaw86r |
| p0037 | Corn V5 Stage** Roots Infested With Corn Root Worm | p0037.crwak74r |
| p0043 | Corn Hybrid (Crusader) Shoot Culture | p0043.cimao89r |
| p0044 | Corn Pedicel 20 Days After Pollination | p0044.cjrag28r |
| p0072 | Corn Mesocotyl 14 Days After Planting Etiolated Seedling | p0072.comfk14r p0072.comft16r |
| p0076 | Corn V6–V7 Stage** Whorl and Leaf Tissue Following ECB1 Infestation | p0076.cwhan08r |
| p0117 | Expanding Internodes 5–9 from Corn Plants Sampled at V10 Stage. Screened 1 | p0117.chcln34r |
| p0118 | Corn Stem Tissue Pooled From the 4–5 Internodes Subtending The Tassel At Stages V8–V12, Night Harvested Screened 1 | p0118.chsbe01r |
| rl0n | Rice 15 Day Old Leaf* | rl0n.pk089.g16 |

TABLE 2-continued cDNA Libraries from Corn, Rice, Soybean and Wheat

| Library | Tissue | Clone |
| --- | --- | --- |
| rlr6 | Rice Leaf 15 Days After Germination, 6 Hours After Infection of Strain *Magaporthe grisea* 4360-R-62 (AVR2-YAMO); Resistant | rlr6.pk0079.d12 |
| rr1 | Rice Root of Two Week Old Developing Seedling | rr1.pk0032.d4 |
| rsl1n | Rice 15-Day-Old Seedling* | rsl1n.pk006.j2 |
| sdp3c | Soybean Developing Pods (8–9 mm) | sdp3c.pk010.f19 |
| ses2w | Soybean Embryogenic Suspension 2 Weeks After Subculture | ses2w.pk0002.e5 |
| sl2 | Soybean Two-Week-Old Developing Seedlings Treated With 2.5 ppm chlorimuron | sl2.pk0099.g8 |
| sr1 | Soybean Root | sr1.pk0107.d1 |
| src2c | Soybean 8 Day Old Root Infected With Cyst Nematode | src2c.pk020.g23 |
| sre | Soybean Root Elongation Zone 4 to 5 Days After Germination | sre.pk0032.d4 |
| wdk3c | Wheat Developing Kernel, 14 Days After Anthesis | wdk3c.pk005.g5 |
| wl1n | Wheat Leaf From 7 Day Old Seedling* | wl1n.pk0132.f6 |
| wlk1 | Wheat Seedlings 1 Hour After Treatment With Herbicide*** | wlk1.pk0001.g3 |
| wlk4 | Wheat Seedlings 4 Hours After Treatment With Herbicide*** | wlk4.pk0023.a11 |
| wre1n | Wheat Root From 7 Day Old Etiolated Seedling* | wre1n.pk0014.c1 |

*These libraries were normalized essentially as described in U.S. Pat. No. 5,482,845, incorporated herein by reference.
**Corn developmental stages are explained in the publication "How a corn plant develops" from the Iowa State University Coop. Ext. Service Special Report No. 48 reprinted June 1993.
***Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding branched-chain amino acid degradation enzymes were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding 3-Hydroxyisobutyrate Dehydrogenase Homologs The BLASTX search using the EST sequences from clones listed in Table 3 revealed similarity of the polypeptides encoded by the cDNAs to 3-hydroxyisobutyrate dehydrogenase homologs from *Helicobacter pylori* J99, *Aquifex aeolicus* or *Rattus norvegicus* (NCBI General Identifier Nos. 4155128, 2982783 and 416873, respectively). Shown in Table 3 are the BLAST results for the sequences of the entire cDNA inserts comprising the indicated cDNA clones ("FIS"), contigs assembled from two or more ESTs ("Contig"), or contigs assembled from an FIS and one or more ESTs ("Contig*"):

TABLE 3

BLAST Results for Sequences Encoding Polypeptides Homologous to 3-Hydroxyisobutyrate Dehydrogenase Homologs

| Clone | Status | NCBI General Identifier No. | BLAST pLog Score |
| --- | --- | --- | --- |
| Contig of:<br>cen3n.pk0138.e1<br>cta1n.pk0052.d10<br>p0037.crwak74r | Contig | 4155128 | 36.00 |
| Contig of:<br>cr1n.pk0191.b10<br>p0076.cwhan08r<br>p0118.chsbe01r | Contig* | 2982783 | 45.00 |
| rr1.pk0032.d4 | FIS | 416873 | 69.70 |
| ses2w.pk0002.e5 | FIS | 4155128 | 42.15 |
| Contig of:<br>sl2.pk0099.g8<br>src2c.pk020.g23 | Contig* | 416873 | 53.52 |
| Contig of:<br>wdk3c.pk005.g5<br>wlk1.pk0001.g3<br>wre1n.pk0014.c1 | Contig | 416873 | 69.30 |

BLAST scores and probabilities indicate that the nucleic acid fragments comprising the instant cDNA clones encode two entire corn, one entire rice, one entire soybean, one portion of soybean and one entire wheat 3-hydroxyisobutyrate dehydrogenase homologs. These sequences represent the first plant sequences encoding 3-hydroxyisobutyrate dehydrogenase homologs.

Example 4

Characterization of cDNA Clones Encoding Hydroxymethylglutaryl-CoA Lyase

The BLASTX search using the EST sequences from clones listed in Table 4 revealed similarity of the polypeptides encoded by the cDNAs to HMG-CoA lyase from *Arabidopsis thaliana* (NCBI General Identifier No. 3426048). Shown in Table 4 are the BLAST results for individual ESTs ("EST"), the sequences of the entire cDNA inserts comprising the indicated cDNA clones ("FIS") contigs assembled from two or more ESTs ("Contig"), orcontigs assembled from an FIS and one or more ESTs ("Contig*"):

TABLE 4

BLAST Results for Sequences Encoding Polypeptides Homologous to Hydroxymethylglutaryl-CoA Lyase

| Clone | Status | BLAST pLog Score 3426048 |
|---|---|---|
| Contig of: | Contig | 124.00 |
| cbn10.pk0004.g10 | | |
| cbn10.pk0031.a5 | | |
| cco1n.pk062.k1 | | |
| cct1c.pk001.c19 | | |
| csi1n.pk0050.f7 | | |
| p0043.cimao89r | | |
| p0044.cjrag28r | | |
| p0072.comfk14r | | |
| p0072.comft16r | | |
| Contig of: | Contig* | 133.00 |
| cbn10.pk0039.e6 | | |
| cen3n.pk0107.b6 | | |
| p0031.ccmaw86r | | |
| p0117.chcln34r | | |
| rl0n.pk089.g16 | FIS | 138.00 |
| rsl1n.pk006.j2 | EST | 142.00 |
| sdp3c.pk010.f19 | EST | 172.00 |
| sre.pk0032.d4 | FIS | 132.00 |
| wl1n.pk0132.f6 | FIS | 67.30 |

The nucleotide sequence from rice clone rsl1n.pk006.j2 is 94.6% identical to a rice EST having NCBI General identifier No. 3759876. The same rice clone is 88.6% identical to another rice EST having NCBI General identifier No. 3759875.

BLAST scores and probabilities indicate that the nucleic acid fragments comprising the instant cDNA clones encode a portion of a wheat HMG-CoA lyase, a substantial portion of two soybean HMG-CoA lyases, two entire or almost entire corn, and two entire or almost entire rice HMG-CoA lyases. These sequences represent a rice variant and the first corn, soybean and wheat sequences encoding HMG-CoA lyase.

Example 5

Characterization of cDNA Clones Encoding Isovaleryl-CoA Dehydrogenase

The BLASTX search using the EST sequences from clones listed in Table 5 revealed similarity of the polypeptides encoded by the cDNAs to isovaleryl-CoA dehydrogenase from *Arabidopsis thaliana* (NCBI General Identifier No. 4995051). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to Isovaleryl-CoA Dehydrogenase

| Clone | Status | BLAST pLog Score 4995051 |
|---|---|---|
| cbn10.pk0034.e3 | FIS | 137.00 |
| rlr6.pk0079.d12 | FIS | 254.00 |
| sr1.pk0107.d1 | EST | 254.00 |
| wlk4.pk0023.a11 | FIS | 106.00 |

BLAST scores and probabilities indicate that the nucleic acid fragments comprising the instant cDNA clones encode a portion of corn, an entire rice, an entire soybean and a substantial portion of a wheat isovaleryl-CoA dehydrogenase. These sequences represent the first corn, rice, soybean and wheat sequences encoding isovaleryl-CoA dehydrogenase.

Example 6

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, VA. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of 30 $\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7

Expression of Chimeric Genes in Dicot Cells

A seed-specific expression cassette composed of the promoter and transcription terminator from the gene encoding the $\beta$ subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis. For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 9

Evaluating Compounds for Their Ability to Inhibit the Activity of Branched-Chain Amino Acid Degradation Enzymes The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity.

What is claimed is:

1. An isolated polynucleotide that encodes a 3-hydroxyisobutyrate dehydrogenase polypeptide having a sequence selected from the group consisting of SEQ ID NOs: 4, 6, 8, and 12.

2. The polynucleotide of claim 1, wherein the polynucleotide comprises a nucleotide sequence selected from the group consisting of SEQ ID NO: 3, 5, 7, and 11.

3. An isolated complement of the polynucleotide of claim 1, wherein (a) the complement and the polynucleotide consist of the same number of nucleotides, and (b) the nucleotide sequences of the complement and the polynucleotide have 100% complementarity.

4. An isolated nucleic acid molecule that (1) encodes a 3-hydroxyisobutyrate dehydrogenase and (2) remain hybridized with the isolated polynucleotide of claim 1 under a wash condition of 0.1×SSC, 0.1% SDS, and 65° C.

5. A cell comprising the polynucleotide of claim 1.

6. The cell of claim 5, wherein the cell is selected from the group consisting of a yeast cell, a bacterial cell and a plant cell.

7. A transgenic plant comprising the polynucleotide of claim 1.

8. A method for transforming a cell comprising introducing into a cell the polynucleotide of claim 1.

9. A method for producing a transgenic plant comprising (a) transforming a plant cell with the polynucleotide of claim 1, and (b) regenerating a plant from the transformed plant cell.

10. A chimeric gene comprising the polynucleotide of claim 1 operably linked to at least one suitable regulatory sequence.

11. A method for altering the level of 3-hydroxyisobutyrate dehydrogenase expression in a host cell, the method comprising:

(1) Transforming a host cell with the chimeric gene of claim 10; and (2) Growing the transformed cell in step (a) under conditions suitable for the expression of the chimeric gene.

* * * * *